United States Patent
Stone et al.

(10) Patent No.: US 6,758,865 B1
(45) Date of Patent: Jul. 6, 2004

(54) SOFT TISSUE XENOGRAFTS

(75) Inventors: Kevin R. Stone, Mill Valley, CA (US); Uri Galili, Chicago, IL (US)

(73) Assignee: CrossCart, Inc., San Francisco, CA (US)

(*) Notice: Subject to any disclaimer, the term of this patent is extended or adjusted under 35 U.S.C. 154(b) by 0 days.

(21) Appl. No.: 09/623,729

(22) PCT Filed: May 27, 1998

(86) PCT No.: PCT/US98/10742

§ 371 (c)(1), (2), (4) Date: Feb. 26, 2001

(87) PCT Pub. No.: WO99/44533

PCT Pub. Date: Sep. 10, 1999

(51) Int. Cl.[7] .................................................. A61F 2/36

(52) U.S. Cl. .............................. 623/23.72; 623/11.11; 623/13.17; 623/14.12; 623/915

(58) Field of Search ........................... 623/11.11, 13.11, 623/13.17, 14.12, 23.72, 66.1, 915, 920, 925; 600/36; 435/1.1, 1.3; 530/350, 356; 8/94.11; 424/422, 423, 548, 572

(56) References Cited

U.S. PATENT DOCUMENTS

| | | | |
|---|---|---|---|
| 4,034,418 A | 7/1977 | Jackson et al. | 3/1.911 |
| 4,344,193 A | 8/1982 | Kenny | 3/1.911 |
| 4,400,833 A | 8/1983 | Kurland | 3/1 |
| 4,502,161 A | 3/1985 | Wall | 3/1.91 |
| 4,597,266 A | 7/1986 | Entrekin | 62/46 |
| 4,609,627 A | 9/1986 | Goldstein | 435/269 |
| 4,627,853 A | 12/1986 | Campbell et al. | 623/16 |
| 4,642,120 A | 2/1987 | Nevo et al. | 623/16 |
| 4,755,593 A | 7/1988 | Lauren | 530/356 |
| 4,776,853 A | 10/1988 | Klement et al. | 8/94.11 |

(List continued on next page.)

FOREIGN PATENT DOCUMENTS

| | | |
|---|---|---|
| EP | 347496 | 12/1989 |
| WO | WO 84/03036 | 8/1984 |
| WO | WO 95/26740 | 10/1995 |
| WO | WO 95/28412 | 10/1995 |
| WO | WO 95/33828 | 12/1995 |

OTHER PUBLICATIONS

Rodrigo et al., "Osteocartilaginous Allografts as Compared with Autografts in the Treatment of Knee Joint Osteocartilaginous Defect in Dogs", Clinical Orthopedics and Related Research, 134, pp. 342–349 (1978).

Sengupta et al., "The Fate of Transplants of Articular Cartilage in the Rabbit", The Journal of Bone and Joint Surgery, 56B, pp. 167–177 (1974).

Webber et al., "Cell Culture of Rabbit Meniscal Fibrochondrocytes: Proliferative and Synthetic Response to Growth Factors and Ascorbate", Journal of Orthopedic Research, 3, pp. 36–42 (1985).

(List continued on next page.)

*Primary Examiner*—David J. Isabella
*Assistant Examiner*—Urmi Chattopadhyay
(74) *Attorney, Agent, or Firm*—McDermott, Will & Emery

(57) ABSTRACT

A method for preparing a soft tissue xenograft includes the steps of removing at least a portion of a soft tissue from a non-human animal to provide a xenograft; washing the xenograft in saline and alcohol; subjecting the xenograft to cellular disruption treatment; and either digesting the xenograft with a glycosidase or glycosidase digestion followed by treatment for sialylation. A soft tissue xenograft for implantation into a human includes a portion of a soft tissue from a non-human animal, wherein the portion has extracellular matrix and substantially only dead cells. The matrix and dead cells have substantially no surface α-galactosyl moieties and have sialic acid molecules linked to at least a portion of surface carbohydrate moieties. Each of the xenografts of the invention has substantially the same mechanical properties as a corresponding native soft tissue.

11 Claims, 8 Drawing Sheets

U.S. PATENT DOCUMENTS

| | | | |
|---|---|---|---|
| 4,789,663 A | 12/1988 | Wallace et al. ............... | 514/21 |
| 4,801,299 A | 1/1989 | Brendel et al. | |
| 4,846,835 A | 7/1989 | Grande ......................... | 623/11 |
| 4,880,429 A | 11/1989 | Stone ........................... | 623/18 |
| 4,902,295 A | 2/1990 | Walthall et al. .......... | 623/23.72 |
| 4,932,973 A | 6/1990 | Gendler ....................... | 623/16 |
| 5,007,934 A | 4/1991 | Stone ........................... | 623/20 |
| 5,067,962 A | 11/1991 | Campbell et al. ............. | 623/13 |
| 5,071,741 A | 12/1991 | Brockbank .................... | 435/1 |
| 5,078,744 A | 1/1992 | Chvapil ........................ | 623/13 |
| 5,092,894 A | 3/1992 | Kenny .......................... | 623/18 |
| 5,116,374 A | 5/1992 | Stone ........................... | 623/16 |
| 5,131,850 A | 7/1992 | Brockbank .................... | 435/1 |
| 5,158,574 A | 10/1992 | Stone ........................... | 623/66 |
| 5,160,313 A | 11/1992 | Carpenter et al. ............ | 600/36 |
| 5,171,273 A | 12/1992 | Silver et al. .................. | 623/13 |
| 5,171,322 A | 12/1992 | Kenny .......................... | 623/18 |
| 5,171,660 A | 12/1992 | Carpenter et al. ............. | 435/1 |
| 5,192,312 A | 3/1993 | Orton ........................... | 623/2 |
| 5,206,023 A | 4/1993 | Hunziker ..................... | 424/423 |
| 5,216,126 A | 6/1993 | Cox et al. .................... | 530/350 |
| 5,263,984 A | 11/1993 | Li et al. ........................ | 623/15 |
| 5,306,311 A | 4/1994 | Stone et al. .................. | 623/18 |
| 5,352,463 A | 10/1994 | Badylak et al. .............. | 424/551 |
| 5,358,525 A | 10/1994 | Fox et al. ..................... | 623/18 |
| 5,507,810 A | 4/1996 | Prewett et al. ................ | 623/11 |
| 5,516,532 A | 5/1996 | Atala et al. ................... | 424/548 |
| 5,521,087 A | 5/1996 | Lee et al. ................. | 435/240.2 |
| 5,613,982 A | 3/1997 | Goldstein ..................... | 623/11 |
| 5,632,778 A | 5/1997 | Goldstein ..................... | 623/11 |
| 5,782,915 A | 7/1998 | Stone ........................... | 623/11 |
| 5,863,296 A | 1/1999 | Orton ........................... | 623/15 |
| 5,865,849 A | 2/1999 | Stone ........................... | 623/18 |
| 5,902,338 A | 5/1999 | Stone ........................... | 623/13 |
| 5,904,716 A | 5/1999 | Gendler ....................... | 623/11 |
| 5,913,900 A | 6/1999 | Stone ........................... | 623/20 |
| 5,922,027 A | 7/1999 | Stone ........................... | 623/11 |
| 5,944,755 A | 8/1999 | Stone ........................... | 623/16 |
| 5,984,858 A | 11/1999 | Stone ........................... | 600/20 |
| 6,046,379 A | 4/2000 | Stone et al. ................... | 623/11 |
| 6,049,025 A | 4/2000 | Stone et al. ................. | 128/898 |
| 6,110,206 A | 8/2000 | Stone ....................... | 623/13.11 |
| 6,210,440 B1 * | 4/2001 | Stone et al. ............. | 623/13.11 |
| 6,402,783 B1 * | 6/2002 | Stone ...................... | 623/13.17 |

OTHER PUBLICATIONS

Rubak et al., "Chondrogenesis in Repair of Articular Cartilage Defects by Free Periosteal Grafts in Rabbits", Acta Orthop. Scand, 53, pp. 181–186 (1982).

Engkvist, Ove, "Reconstruction of Patellar Articular Cartilage with Free Autologous Perichondrial Grafts", Scand. J. Plast. Reconstr. Surg., 13, pp. 361–369 (1979).

Collins et al., "Characterization of Porcine Endothelial Cell Determinants Recognized by Human Natural Antibodies", Xenotransplantation, 1, pp. 36–46 (1994).

Satake et al., "Limited Specificity of Xenoantibodies In Diabetic Patients Transplanted With Fetal Porcine Islet Cell Clusters. Main Anitbody Reactivity Against α–linked Galactose–Containing Epitopes", Xenotransplanation, 1, pp. 89–101 (1994).

LaVecchio et al., "Enzymatic Removal of Alpha–Galactosyl Epitopes From Porcine Endothelial Cells Diminishes The Cytotoxic Effect of Natural Antibodies", Transplantation, 60, pp. 841–847(1995).

Stone et al., "Surgical Technique of Meniscal Replacement", Arthroscopy: The Journal of Arthroscopic and Related Surgery, 9, pp. 234–237 (1993).

Cotterell et al., "The Humoral Immune Response in Humans Following Cross–Perfusion of Porcine Organs", Transplantation, 60, pp. 861–868 (1995).

Galili, "Interaction of the Natural Anti–Gal Antibody with α–Galactosyl Epitodes: a Major Obstacle for Xenotransplantation in Humans", Immunology Today, 14, pp. 480–482 (1993).

Elves et al., "An Investigation Into The Immunogenicity Of Various Components of Osteoarticular Grafts", The British Journal of Experimental Pathology, 55, pp. 344–351 (1974).

Derby et al., "The Histochemical Specificity of Streptomyces Hyaluronidase and Chondroitinase ABC", Histochemical Journal, 10, pp. 529–547 (1978).

Homandberg et al., "High Concentrations of Fibronectin Fragments Cause Short–Term Catabolic Effects in Cartilage Tissue While Lower Concentrations Cause Continuous Anabolic Effects", Archives of Biochemistry and Biophysics, 311:2, pp. 213–218 (1994).

Homandberg et al., "Agents That Block Fibronectin Fragment–Mediated Cartilage Damage Also Promote Repair", Inflamm. Res., 46, pp. 467–471 (1997).

Homandberg et al., "Exposure of Cartilage to a Fibronectin Fragment Amplifies Catabolic Processes While Also Enhancing Anabolic Processes to Limit Damage", Journal of Orthopaedic Research, 16, pp. 237–246 (1998).

Homandberg et al., "Hyaluronic Acid Suppresses Fibronectin Fragment Mediated Cartilage Chondrolysis: I. In vitro", Osteoarthritis and Cartilage 5, pp. 309–319 (1997).

Homandberg et al., "Association of Proteoglycan Degradation with Catabolic Cytokine and Stromelysin Release from Cartilage Cultured with Fibronectin Fragments", 334:2, pp. 325–331 (1996).

Homandberg et al., "Potential Regulation of Cartilage Metabolism in Osteoarthritis by Fibronectin Fragments".

Homandberg et al. "Fibronectin–Fragment–Induced Cartilage Chondrolysis is Associated with Release of Catabolic Cytokines", Biochem J. 321, pp. 751–757, (Great Britain) (1997).

Homandberg et al., "Cartilage Damaging Activities of Fibronectin Fragments Derived from Cartilage and Synovial Fluid", Osteoarthritis and Cartilage 6, pp. 231–244 (1998).

Homandberg et al., "Cartilage Chondrolysis by Fibronectin Fragments Causes Cleavage of Aggrecan at the Same Site as Found in Osteoarthritic Cartilage", Osteoarthritis and Cartilage 5, pp. 450–453 (1997).

Homandberg et al., "Fibronectin Fragment Mediated Cartilage Chondrolysis. I. Suppression by Anti–Oxidants", *BBA Biochimica et Biophysica Acta*, 1317, pp. 132–142 (1996).

Homandberg et al., "Fibronectin Fragment Mediated Cartilage Chondrolysis. II. Reparative Effects of Anti–Oxidants", *BBA Biochimica et Biophysica Acta*, 1317, pp. 143–148 (1996).

Kang et al., "Cultured Human Ankle and Knee Cartilage Differ in Susceptibility to Damage Mediated by Fibronectin Fragments", Journal of Orthopaedic Research, 16, pp. 551–556 (1998).

Lipman et al., "Xenografts of Articular Chondrocytes in the Nude Mouse", Calcif. Tissue Int., 35, pp. 767–772 (1983).

Williams et al., "Hyaluronic Acid Suppresses Fibronectin Fragment Mediated Cartilage Chondrolysis: II. In vitro", Osteoarthritis and Cartilage, 5, pp. 235–240 (1997).

Zhu et al., "Viscoelastic Shear Properties of Articular Cartilage and the Effects of Glycosidase Treatments", Journal of Orthopaedic Research, 11, pp. 771–781 (1993).

Ionescu et al., "Heart Valve Replacement with the Ionescu–Shiley Pericardial Xenograft", J. Thorac. Cardiovas. Surg., 73, pp. 31–42 (1977).

Stone et al., "Porcine and Bovine Cartilage Transplants in Cynomolgus Monkey: I. A Model for Chronic Xenograft Rejection", Transplantation, 63, pp. 640–645 (1997).

Galili et al., "Porcine and Bovine Cartilage Transplants in Cynomolgus Monkey: II. Changes in Anti–Gal Response During Chronic Rejection", Transplantation, 63, pp. 646–651 (1997).

Stedman's Medical Dictionary, Williams & Wilkins, 26 ed., pp. 793, 1966 (1995).

Galili et al., "Man, Apes, and Old World Monkeys Differ from Other Mammals in the Expression of $\alpha$—Galactosyl Epitopes on Nucleated Cells", J. Biol. Chem., 263, 17755–17762 (1988).

Fadali et al., "The Use of Autogenous Peritoneum for Heart Valve Replacement", J. Thorac. Cardiovas. Surg., 60, pp. 188–195 (8/70).

Woodroof,"The Chemistry and Biology of Aldehyde Treated Tissue Heart Valve Heterografts", pp. 349–352.

U. Galili et al., "Interaction Between Human Natural Anit–$\alpha$–Galactosyl Immunoglobulin G and Bacteria Of The Human Flora", Infect. Immun. 56, 1730–1737 (1988).

R.M. Hamadeh et al., "Human Natural Anti–Gal IgG Regulates Alternative Complement Pathway Activation on Bacterial Surfaces", J. Clin. Invest. 89, 1223–1235 (1992).

M. Sandrin et al., "Anti–Pig IgM Antibodies in Human Serum React Predominantly With Gal (al–3) Gal Epitodes", Proc. Natl. Acad. Sci USA 90, 11391–11395 (1993).

H. Good et al., "Identification of Carbohydrate Structures That Bind Human Antiporcine Antibodies: Implications for Discordant Xenografting in Humans", Transplant. Proc. 24, 559–562 (1992).

B.H. Collins, et al., "Cardiac Xenografts Between Primate Species Provide Evidence for the Importance of the $\alpha$–Galactosyl Determinant in Hyperacute Rejection", J. Immunol. 154, 5500–5510 (1995).

R.G. Spiro et al., "Occurrence of $\alpha$–D–Galactosyl Residues in the Thyroglobulin from Several Species. Localization in the Saccharide Chains of Complex Carbohydrate Units", 259 J. Biol. Chem. 259, 9858–66 (1984).

R.G. Arumugham et al., "Structures of the Asparagine–Linked Sugar Chains of Laminin", Biochem. Biophys. Acta 883, 112–126 (1986).

* cited by examiner

SOFT TISSUE XENOGRAFTS

FIELD OF THE INVENTION

The present invention relates to the field of treatment of defective human knee joints, and in particular, to replacement and repair of defective or damaged human knee joint soft tissue using a substantially immunologically compatible soft tissue from a non-human animal.

BACKGROUND OF THE INVENTION

The human knee is a complex joint containing spatially interrelated bones, and soft tissue which interact to create a variety of motions.

The term "soft tissue", as used herein, refers to cartilaginous structures, such as meniscus and articular cartilage; and ligaments, such as anterior cruciate ligaments; and tendons.

Meniscus Cartilage

Specifically, the femoral condyles articulate with the surface plateaus of the tibia, through the cartilaginous medial and lateral menisci soft tissue, and all of these structures are held in place by various ligaments. The medial and lateral menisci are structures comprised of cells called fibrochondrocytes and an extracellular matrix of collagen and elastic fibers as well as a variety of proteoglycans. Undamaged menisci provide shock absorption for the knee by ensuring proper force distribution, stabilization, and lubrication for the interacting bone surfaces within the knee joint, which are routinely exposed to repeated compression loading during normal activity. Much of the shock absorbing function of the medial and lateral menisci is derived from the elastic properties inherent to cartilage. When menisci are damaged through injury, disease, or inflammation, arthritic changes occur in the knee joint, with consequent loss of function.

Since joint cartilage in adults does not naturally regenerate to a significant degree once it is destroyed, damaged adult menisci have historically been treated by a variety of surgical interventions. Damaged menisci have been removed and replaced with prosthetic devices. An artificial knee joint having a rigid plastic femoral member and a metal tibial member is disclosed in U.S. Pat. No. 4,034,418. A number of meniscus prostheses have been devised which employ resilient materials such as silicone rubber or natural rubber, as in U.S. Pat. No. 4,344,193 and U.S. Pat. No. 4,502,161. Additional deformable, flexible resilient materials for a meniscus prosthesis such as collagen, tendon, or fibrocartilage are disclosed in U.S. Pat. No. 5,092,894 and U.S. Pat. No. 5,171,322. A cartilage replacement apparatus constructed of polyethylene plastic filled with small ball bearings or gelatinous fluid is described in U.S. Pat. No. 5,358,525. However, the known artificial prostheses have been unsatisfactory for treatment of damaged menisci, since they are deficient in the elastic, and therefore in the shock-absorbing, properties characteristic of natural menisci. Moreover, the known artificial devices have not proven able to withstand the forces inherent to routine knee joint function.

One of the present inventors provided improved prosthetic menisci in several of his earlier patents (U.S. Pat. No. 4,880,429; U.S. Pat. No. 5,007,934; U.S. Pat. No. 5,116,374; and U.S. Pat. No. 5,158,574). These patents generally disclose prosthetic menisci formulated from dry, porous matrices of processed natural fibers such as reconstituted cross-linked collagen, which optionally include glycosaminoglycan molecules. Generally, the source of collagen for these prosthetic menisci has been animal Achilles tendons or skin. The reconstitution process removes non-collagenous materials such as glycoproteins, proteoglycans, lipids, native glycosaminoglycans, and the like, which may confer additional elastic properties to the original tissue.

Articular Cartilage

Articular cartilage soft tissue covers the ends of all bones that form articulating joints in humans and animals. Articular cartilage is made of fibrochondrocytes and an extracellular matrix of collagen fibers as well as a variety of proteoglycans. The cartilage acts in the joint as a mechanism for force distribution and as a lubricant in the area of contact between the bones. Without articular cartilage, stress concentration and friction would occur to the degree that the joint would not permit ease of motion. Loss of the articular cartilage usually leads to painful arthritis and decreased joint motion.

Damaged adult articular cartilage has historically been treated by a variety of surgical interventions including repair, replacement, or by excision. With repair or excision, regeneration of tissue may occur, although the tissue is usually temporary and inadequate to withstand the normal joint forces.

Replacement of articular cartilage usually has been by allografting (Sengupta et al. (1974) *J. Bone Suro.* 56B(1): 167–177; Rodrigo et al. (1978) *Clin Orth.* 134:342–349) by periosteal grafts (see, e.g., Engkvist (1979) *Scan J. Plast. Reconstr. Suro.* 13:361–369; Rubak (1982) *Acta Orthop. Scan.* 53:181–186) or with metal and/or plastic components (Rubash et al., eds. (1991) *Clin. Orth. Rel. Res.* 271:2–96). Allografting dead cartilage tissue has been tried for years with minimal success. This approach has been only partially successful over the long term due to the host's immunologic response to the graft, failures in the cryopreservation process, and failures of the attachment sites. Replacement of an entire joint surface with metal and plastic components has met excellent success for the older, more sedentary patients, but is generally considered insufficient for tolerating the impact of athletic activities, and has not been shown to restore normal joint mechanics.

In alternative prior art approaches, articular cartilage has been replaced with prostheses composed of bone and/or artificial materials. For example, U.S. Pat. No. 4,627,853 describes the use of demineralized allogenic or xenogenic bone segments as replacements. The proper functioning of these replacements depends on the differential demineralization of the bone segments. U.S. Pat. No. 4,846,835 describes a grafting technique for transplantation of fibrochondrocytes to promote healing lesions in articular cartilage. U.S. Pat. No. 4,642,120 describes the use of gel-like compositions containing embryonal fibrochondrocytes. U.S. Pat. No. 5,306,311 describes a prosthetic articular cartilage which includes a dry, porous volume matrix adapted to have in vivo an outer contour substantially the same as that of natural articular cartilage.

Despite these developments, the replacement of articular cartilage soft tissue with structures consisting of permanent artificial materials generally has been less than satisfactory, and a structure suitable as articular cartilage and constructed from natural resorbable materials, or analogs thereof, has not been developed. Because the opposing articular cartilage of mammalian joints is so fragile, it will not withstand abrasive interfaces nor compliance variances from normal which eventually result from the implantation of prior art artificial cartilage. Additionally, joint forces are multiples of body weight which, in the case of the knee and hip, are typically encountered over a million cycles per year. Thus far, prior art permanent artificial cartilages have not been composed of materials having natural articular cartilage properties, nor have they been able to be positioned securely enough to withstand such routine forces.

Ligaments

Anterior cruciate ligament soft tissue of the knee (hereinafter the ACL) functions to resist anterior displacement of the tibia from the femur at all flexion positions. The ACL also resists hyperextension and contributes to rotational stability of the fully extended knee during internal and external tibial rotation. The ACL may play a role in proprioception. The ACL is made up of connective tissue structures composed of cells, water, collagen, proteoglycans, fibronectin, elastin, and other glycoproteins. Cyril Frank, M. D. et al., *Normal Ligament: Structure, Function, and Composition. Injury and Repair of the Musculoskeletal Soft Tissues*, 2:45–101. Structurally, the ACL attaches to a depression in the front of the intercondyloid reminence of the tibia extending postero-superiorly to the medial wall of the lateral femoral condyle.

The preferred treatment of damaged ACL is ligament reconstruction, using a bone-ligament-bone autograft. Cruciate ligament reconstruction has the advantage of immediate stability and a potential for immediate vigorous rehabilitation. However, the disadvantages to ACL reconstruction are significant: for example, normal anatomy is disrupted when the patellar tendon or hamstring tendons are used for the reconstruction; placement of intraaticular hardware is required for ligament fixation; and anterior knee pain frequently occurs. Moreover, recent reviews of cruciate ligament reconstruction indicate an increased risk of degenerative arthritis with intruarticular ACL reconstruction in large groups of patients.

A second method of treating ACL injuries, referred to as "primary repair", involves suturing the torn structure back into place. Primary ACL repair has the potential advantages of a limited arthroscopic approach, minimal disruption of normal anatomy, and an out-patient procedure under a local anesthetic. The potential disadvantage of primary cruciate ligament repair is the perception that over the long term ACL repairs do not provide stability in a sufficient number of patients, and that subsequent reconstruction may be required at a later date. The success rate of anterior cruciate ligament repair has generally hovered in the 60% to 70% range.

Xenografts

Much of the structure and many of the properties of original soft tissues may be retained in transplants through use of heterograft or xenograft materials, that is, soft tissue from a different species than the graft recipient. For example, tendons or ligaments from cows or other animals are covered with a synthetic mesh and transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, burn and other wound dressings is disclosed in U.S. Pat. No. 4,755,593. Bovine, ovine, or porcine blood vessel xenografts are disclosed in WO 84/03036. However, none of these disclosures describe the use of a xenograft for soft tissue replacement.

Once implanted in an individual, a xenograft provokes immunogenic reactions such as chronic and hyperacute rejection of the xenograft. The term "chronic rejection", as used herein refers to an immunological reaction in an individual against a xenograft being implanted into the individual. Typically, chronic rejection is mediated by the interaction of IgG natural antibodies in the serum of the individual receiving the xenograft and carbohydrate moieties expressed on cells, and/or cellular matrices and/or extracellular components of the xenograft. For example, transplantation of soft tissue cartilage xenografts from non-primate mammals (e.g., porcine or bovine origin) into humans is primarily prevented by the interactions between the IgG natural anti-Gal antibody present in the serum of humans with the carbohydrate structure Gal$\alpha$1-3Gal$\beta$1-4GlcNAc-R ($\alpha$-galactosyl or $\alpha$-gal epitope) expressed in the xenograft. K. R. Stone et al., *Porcine and bovine cartilage transplants in cynomolgus monkey: I. A model for chronic xenograft rejection*, 63 Transplantation 640–645 (1997); U. Galili et al., *Porcine and bovine cartilage transplants in cynomolgus monkey: II. Changes in anti-Gal response during chronic rejection*, 63 Transplantation 646–651 (1997). In chronic rejection, the immune system typically responds within one to two weeks of implantation of the xenograft.

In contrast with "chronic rejection", "hyper acute rejection" as used herein, refers to the immunological reaction in an individual against a xenograft being implanted into the individual, where the rejection is typically mediated by the interaction of IgM natural antibodies in the serum of the individual receiving the xenograft and carbohydrate moieties expressed on cells. This interaction activates the complement system causing lysis of the vascular bed and stoppage of blood flow in the receiving individual within minutes to two to three hours.

The term "extracellular components", as used herein, refers to any extracellular water, collagen and elastic fibers, proteoglycans, fibronectin, elastin, and other glycoproteins, which are present in soft tissue.

Xenograft materials may be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional crosslinking through the side chain carboxyl groups of aspartic and glutamic acid residues of the collagen polypeptide. Glutaraldehyde and diamine tanning also increases the stability of the xenograft tissue.

Xenograft tissues may also be subjected to various physical treatments in preparation for implantation. For example, U.S. Pat. No. 4,755,593 discloses subjecting xenograft tissue to mechanical strain by stretching to produce a thinner and stiffer biomaterial for grafting. Tissue for allograft transplantation is commonly cryopreserved to optimize cell viability during storage, as disclosed, for example, in U.S. Pat. No. 5,071,741; U.S. Pat. No. 5,131,850; U.S. Pat. No. 5,160,313; and U.S. Pat. No. 5,171,660. U.S. Pat. No. 5,071,741 discloses that freezing tissues causes mechanical injuries to cells therein because of extracellular or intracellular ice crystal formation and osmotic dehydration.

SUMMARY OF THE INVENTION

The present invention provides a substantially non-immunogenic soft tissue xenograft for implantation into a human in need of soft tissue repair or replacement. The invention further provides methods for processing xenogeneic soft tissue with reduced immunogenicity but with substantially native elasticity and load-bearing capabilities for xenografting into humans.

As used herein, the term "xenograft" is synonymous with the term "heterograft" and refers to a graft transferred from an animal of one species to one of another species. Stedman's Medical Dictionary, Williams & Wilkins, Baltimore, Md. (1995).

As used herein, the term "xenogeneic", as in, for example, xenogeneic soft tissue, refers to soft tissue transferred from an animal of one species to one of another species. Id.

The methods of the invention, include, alone or in combination, treatment with radiation, one or more cycles of freezing and thawing, treatment with a chemical cross-linking agent, treatment with alcohol, or ozonation. In addition to or in lieu of these methods, the methods of the invention include a cellular disruption treatment and glycosidase digestion of carbohydrate moieties of the xenograft. Optionally, the glycosidase digestion can be followed by further treatments, such as, for example, treatment of carbohydrate moieties of the xenograft with capping molecules. Further, in addition to or in lieu of these methods, the methods of the invention include a cellular disruption treatment and glycosidase digestion of carbohydrate moieties of the xenograft with a glycosidase in a concentration range of about 1 mU/ml to about 1000 U/ml or glycosidase digestion followed by treatment of the carbohydrate moieties of the xenograft with sialic acid. After one or more of the above-described processing steps, the methods of the invention provide a xenograft having substantially the same mechanical properties as a native soft tissue.

As used herein, the term "cellular disruption" as in, for example, cellular disruption treatment, refers to a treatment for killing cells.

As used herein, the term "capping molecule(s)", refers to molecule(s) which link with carbohydrate chains such that the xenograft is no longer recognized as foreign by the subject's immune system.

In one embodiment, the invention provides an article of manufacture comprising a substantially non-immunogenic soft tissue xenograft for implantation into a human.

In another embodiment, the invention provides a method of preparing a soft tissue xenograft for implantation into a human, which includes removing at least a portion of a soft tissue from a non-human animal to provide a xenograft; washing the xenograft in water and alcohol; and subjecting the xenograft to at least one treatment selected from the group consisting of exposure to ultraviolet radiation, immersion in alcohol, ozonation, and freeze/thaw cycling, whereby the xenograft has substantially the same mechanical properties as a corresponding portion of a native soft tissue.

As used herein, the term "portion", as in, for example, a portion of soft tissue or second surface carbohydrate moieties, refers to all or less than all of the respective soft tissue or second surface carbohydrate moieties.

In another embodiment, the invention provides a method of preparing a soft tissue xenograft for implantation into a human, which includes removing at least a portion of a soft tissue from a non-human animal to provide a xenograft; washing the xenograft in water and alcohol; subjecting the xenograft to a cellular disruption treatment; and digesting the xenograft with a glycosidase to remove first surface carbohydrate moieties, whereby the xenograft has substantially the same properties as a corresponding portion of a native soft tissue, where the glycosidase may be a galactosidase such as an α-galactosidase.

As used herein, the term "first surface carbohydrate moiety (moieties)" refers to a terminal α-galactosyl sugar at the non-reducing end of a carbohydrate chain.

In still other embodiments, this method can include additional steps such as, for example, treating second surface carbohydrate moieties on the xenograft with capping molecules to cap at least a portion of the second surface carbohydrate moieties, whereby the xenograft is substantially non-immunogenic, and optionally at least a portion of the capping molecules are a plurality of fucosyl molecules or a plurality of n-acetyl glucosamine molecules.

As used herein, the term "second surface carbohydrate moiety (moieties)" refers to a N-acetyllactosamine residue at the non-reducing end of a carbohydrate chain, the residue being non-capped either naturally or as a result of prior cleavage of an α-galactosyl epitope.

In a further embodiment, the invention provides a method of preparing a soft tissue xenograft for implantation into a human, which includes removing at least a portion of soft tissue from a non-human animal to provide a xenograft; washing the xenograft in water and alcohol; subjecting the xenograft to a cellular disruption treatment; and digesting the xenograft with a glycosidase in a concentration range of about 1 milliunit/ml to about 1000 units/ml to remove first surface carbohydrate moieties from the xenograft, whereby the xenograft has substantially the same mechanical properties as a corresponding portion of a native soft tissue, where the glycosidase may be a galactosidase such as an α-galactosidase.

In still a further embodiment, the invention provides a method of preparing a soft tissue xenograft for implantation into a human, which includes removing at least a portion of soft tissue from a non-human animal to provide a xenograft; washing the xenograft in, water and alcohol; subjecting the xenograft to a cellular disruption treatment; digesting the xenograft with a glycosidase to remove first surface carbohydrate moieties from the xenograft; and treating second surface carbohydrate moieties on the xenograft with sialic acid to cap at least a portion of the second surface carbohydrate moieties, whereby the xenograft is substantially non-immunogenic and has substantially the same mechanical properties as a corresponding portion of a native soft tissue, where the glycosidase may be a galactosidase such as an α-galactosidase.

As used herein, the terms "to cap" or "capping", refer to linking a capping molecule such as a carbohydrate unit to the end of a carbohydrate chain, as in, for example, covalently linking a carbohydrate unit to surface carbohydrate moieties on the xenograft.

In yet further embodiments, the invention provides articles of manufacture including substantially non-immunogenic soft tissue xenografts for implantation into humans produced by one or more of the above-identified methods of the invention.

In another embodiment, the invention provides a soft tissue xenograft for implantation into a human which includes a portion of a soft tissue from a non-human animal, wherein the portion has substantially no surface carbohydrate moieties which are susceptible to glycosidase digestion, and whereby the portion has substantially the same mechanical properties as a corresponding portion of a native soft tissue.

In yet another embodiment, the invention provides a soft tissue xenograft for implantation into a human which includes a portion of a soft tissue from a non-human animal, wherein the portion includes an extracellular matrix and substantially only dead cells, the extracellular matrix and the dead cells having substantially no surface α-galactosyl moieties and having sialic acid molecules linked to at least a portion of surface carbohydrate moieties. The portion of the soft tissue is substantially non-immunogenic and has substantially the same mechanical properties as the native soft tissue.

BRIEF DESCRIPTION OF THE DRAWINGS

The various features of the invention may be more fully understood from the following description when read together with the accompanying drawings.

DETAILED DESCRIPTION OF THE PREFERRED EMBODIMENTS

Figure 1:
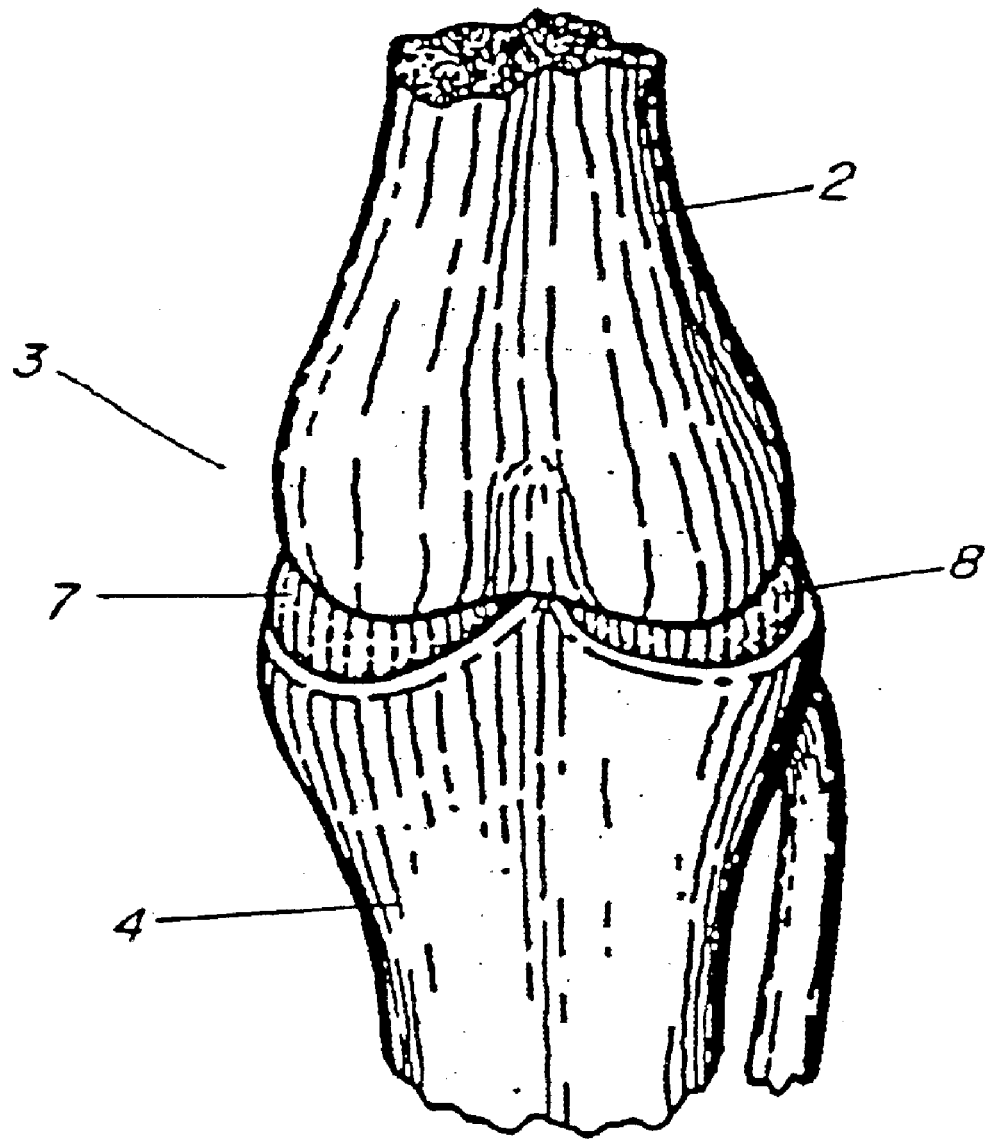
FIG. 1 shows a simplified diagrammatic representation of a human knee joint, with medial and lateral menisci in their native positions.
Figure 2:
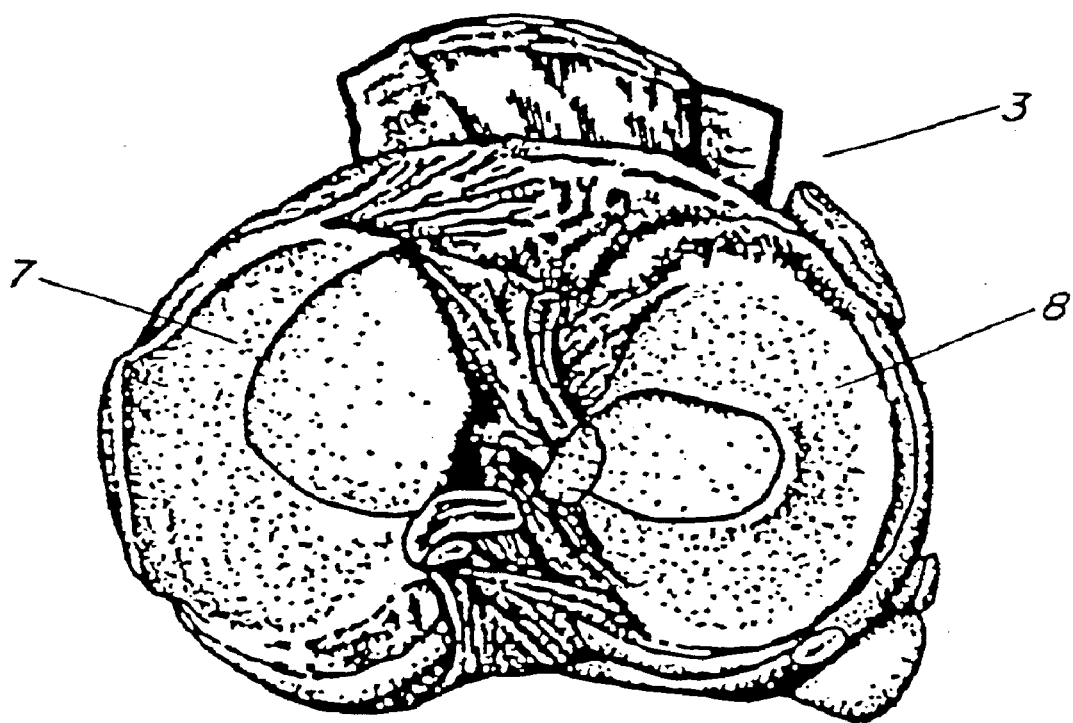
FIG. 2 is a diagrammatic representation of a cut-away view of a human knee joint, showing the medial and lateral menisci as they are positioned in vivo over the medial and lateral condyles of the tibia.

The present invention is directed against the chronic rejection of xenografts for implantation into humans. Accordingly, the soft tissue xenograft produced in accordance with the method of the invention is substantially non-immunogenic, while generally maintaining the mechanical properties of a native soft tissue.

While the soft tissue may undergo some shrinkage during processing, a soft tissue xenograft prepared in accordance with the invention will have the general appearance of a native soft tissue xenograft. For example, a medial meniscus xenograft prepared in accordance with the invention will have the general appearance of a native medial meniscus, and a lateral meniscus xenograft of the invention will have the general appearance of a native lateral meniscus. The soft tissue xenograft may also be cut into segments, each of which may be implanted into a joint of the recipient as set forth below.

The invention provides, in one embodiment, a method for preparing or processing a xenogeneic soft tissue for engraftment into humans. The soft tissue may be harvested from any non-human animal to prepare the xenografts of the invention. Soft tissue from transgenic non-human animals or from genetically altered non-human animals may also be used as xenografts in accordance with the present invention. Preferably, bovine, ovine, or porcine knee joints serve as sources of the medial and lateral menisci and articular cartilage soft tissue used to prepare the xenografts. Preferably, bovine joints serve as the sources of the ligament soft tissue used to prepare the xenografts. More preferably, immature animal joints are the sources of the soft tissue, since the soft tissue of younger animals may be inherently more elastic and engraftable than that of older animals. Most preferably, the age of the source animal is between six and eighteen months at time of slaughter. Additionally, the patellar tendon, the anterior or posterior cruciate ligaments, the Achilles tendon or the hamstring tendons may be harvested from the animal source and used as a donor ligament.

In the first step of the method of the invention, an intact soft tissue is removed from a non-human animal. Medial or lateral meniscus are removed from the knee joints of the non-human animal. Articular cartilage are removed from any joint of the non-human animal. Ligaments and tendons, such as, for example, the Achilles tendon, are also removed from non-human animals. Preferably soft tissue from a corresponding joint is used to make the soft tissue xenograft of the invention. For example, articular cartilage from a femuro-tibial (stifle) joint is used to make an articular cartilage xenograft for implantation into a knee. Similarly, articular cartilage from a donor animal's hip joint is used to make an articular cartilage xenograft for a human hip joint.

The joint which serves as the source of the soft tissue should be collected from freshly killed animals and preferably immediately placed in a suitable sterile isotonic or other tissue preserving solution. Harvesting of the joints should occur as soon as possible after slaughter of the animal and preferably should be performed in the cold, i.e., in the approximate range of about 5° C. to about 20° C., to minimize enzymatic degradation of the soft tissue.

The soft tissue is harvested in the cold, under strict sterile technique.

With respect to meniscal soft tissue, the joint is opened by first transecting the patellar tendon. The horns of the menisci are dissected free of adhering tissue. A small amount of bone representing a substantially cylindrical plug of approximately five millimeters in diameter by five millimeters in depth may be left attached to the horns. The meniscal synovial junction is carefully identified and freed from the meniscus tissue itself, thereby forming the xenograft.

With respect to articular cartilage soft tissue, a fine peel of articular cartilage with a small layer of subchondral bone is shaved from the donor joint to form the xenograft.

With respect to ligament soft tissue, the donor joint is opened by standard surgical technique. Preferably, the ligament is harvested with a block of bone attached to one or both ends, although in some forms of the invention the ligament alone is harvested. In one form of the invention, a block of bone representing a substantially cylindrical plug of approximately 9–10 mm in diameter by approximately 20–40 mm in length may be left attached to the ligament. The ligament is carefully identified and dissected free of adhering tissue, thereby forming the xenograft.

The xenograft is then washed in about ten volumes of sterile cold water to remove residual blood proteins and water soluble materials. The xenograft is then immersed in alcohol at room temperature for about five minutes, to sterilize the tissue and to remove non-collagenous materials.

A meniscus soft tissue xenograft appears as a shiny "C"-shaped fibrous tissue, having generally a crescent-shaped principal surface on the top side (the "superior surface") and a generally crescent-shaped principal surface on the bottom side (the "inferior surface"), where the outer portions of the superior and inferior surfaces are joined by way of an outer lateral surface and the inner portions of the superior and inferior surfaces are joined by way of an inner lateral surface.

The articular cartilage soft tissue xenograft appears as a hyaline tissue supported on a bone substrate, having generally a spherical-shaped principal surface on the tip side (the "superior surface"), with the under surface of the bone (the "inferior surface") being rough.

After alcohol immersion, the xenograft may be directly implanted or may be subjected to at least one of the following treatments: radiation treatment, treatment with alcohol, ozonation, one or more cycles of freezing and thawing, and/or treatment with a chemical cross-linking agent. When more than one of these treatments is applied to the xenograft, the treatments may occur in any order.

In one embodiment of the method of the invention, the xenograft may be treated by exposure to ultraviolet radiation for about fifteen minutes or gamma radiation in an amount of about 0.5 to 3 MegaRad.

In another embodiment, the xenograft may be treated by again being placed in an alcohol solution. Any alcohol solution may be used to perform this treatment. Preferably, the xenograft is placed in a 70% solution of isopropanol at room temperature.

In still another embodiment, the xenograft may be subjected to ozonation.

In a further embodiment of the method of the invention, the xenograft may be treated by freeze/thaw cycling. For example, the xenograft may be frozen using any method of freezing, so long as the xenograft is completely frozen, i.e., no interior warm spots remain which contain unfrozen soft tissue. Preferably, the xenograft is dipped into liquid nitrogen for about five minutes to perform this step of the method. More preferably, the xenograft is frozen slowly by placing it in a freezer. In the next step of the freeze/thaw cycling treatment, the xenograft is thawed by immersion in an isotonic saline bath at room temperature (about 25° C.) for about ten minutes. No external heat or radiation source is used, in order to minimize fiber degradation.

In yet a further embodiment, the xenograft may optionally be exposed to a chemical agent to tan or crosslink the proteins within the extracellular components, to further diminish or reduce the immunogenic determinants present in the xenograft. Any tanning or crosslinking agent may be used for this treatment, and more than one crosslinking step may be performed or more than one crosslinking agent may be used in order to ensure complete crosslinking and thus optimally reduce the immunogenicity of the xenograft. For example, aldehydes such as glutaraldehyde, formaldehyde, adipic dialdehyde, and the like, may be used to crosslink the extracellular collagen of the xenograft in accordance with the method of the invention. Other suitable crosslinking agents include aliphatic and aromatic diamines, carbodiimides, diisocyanates, and the like.

When glutaraldehyde is used as the crosslinking agent, for example, the xenograft may be placed in a buffered solution containing about 0.001% to about 5.0% glutaraldehyde and preferably, about 0.05% to about 5.0% glutaraldehyde, and having a pH of about 7.4. Any suitable buffer may be used, such as phosphate buffered saline or trishydroxymethylaminomethane, and the like, so long as it is possible to maintain control over the pH of the solution for the duration of the crosslinking reaction, which may be from one to fourteen days, and preferably from one to five days, and most preferably from three to five days.

Alternatively, the xenograft can be exposed to a crosslinking agent in a vapor form, including, but not limited to, a vaporized aldehyde crosslinking agent, such as, for example, vaporized formaldehyde. The vaporized crosslinking agent can have a concentration and a pH and the xenograft can be exposed to the vaporized crosslinking agent for a period of time suitable to permit the crosslinking reaction to occur. For example, the xenograft can be exposed to vaporized crosslinking agent having a concentration of about 0.001% to about 5.0% and preferably, about 0.05% to about 5.0%, and a pH of about 7.4, for a period of time which can be from one to fourteen days, and preferably from one to five days, and most preferably from three to five days. Exposure to vaporized crosslinking agent can result in reduced residual chemicals in the xenograft from the crosslinking agent exposure.

The crosslinking reaction should continue until the immunogenic determinants are substantially eliminated from the xenogeneic soft tissue, but the reaction should be terminated prior to significant alterations of the mechanical properties of the xenograft. When diamines are also used as crosslinking agents, the glutaraldehyde crosslinking should occur after the diamine crosslinking, so that any unreacted diamines are capped. After the crosslinking reactions have proceeded to completion as described above, the xenograft should be rinsed to remove residual chemicals, and 0.01–0.10 M glycine, and preferably, 0.01–0.05 M glycine may be added to cap any unreacted aldehyde groups which remain.

In addition to or in lieu of the above treatments, the xenograft can be subjected to a cellular disruption treatment to kill the xenograft's cells, which precedes or follows digestion of the xenograft with glycosidases to remove first surface carbohydrate moieties from the xenograft. The glycosidase concentration is in a range about 1 mU/mi to about 1000 U/ml, and preferably, in the range of about 10 U/ml to about 500 U/ml, and most preferably, in the range of about 100 U/ml to 200 U/ml. The glycosidase digestion in turn can be followed by linkage with capping molecules such as sialic acid to cap surface N-acetyllactosamine ends of carbohydrate chains of the xenograft.

In an embodiment of this method of the invention, the xenograft is subjected to a cellular disruption treatment to kill the cells of the soft tissue prior to in vitro digestion of the xenograft with glycosidases. Typically after surface carbohydrate moieties have been removed from living cells and the extracellular matrix, the living cells reexpress the surface carbohydrate moieties. Reexpression of antigenic moieties of a xenograft can provoke continued immunogenic rejection of the xenograft. In contrast, dead cells are unable to reexpress surface carbohydrate moieties. Removal of antigenic surface carbohydrate moieties from dead cells and the extracellular components of a xenograft substantially permanently eliminates antigenic surface carbohydrate moieties as a source of immunogenic rejection of the xenograft.

Accordingly, in the above-identified embodiment, the xenograft of the present invention is subjected to freeze/thaw cycling as discussed above to disrupt, i.e., to kill the cells of the soft tissue. Alternatively, the xenograft of the present invention is treated with gamma radiation having an amount of 0.2 MegaRad up to about 3 MegaRad. Such radiation kills the soft tissue cells and sterilizes the xenograft. Once killed, the soft tissue cells are no longer able to reexpress antigenic surface carbohydrate moieties such α-gal epitopes which are factors in the immunogenic rejection of the transplanted xenografts.

Either before or after the soft tissue cells are killed, the xenograft is subjected to in vitro digestion of the xenograft with glycosidases, and specifically galactosidases, such as α-galactosidase, to enzymatically eliminate antigenic surface carbohydrate moieties. In particular, α-gal epitopes are eliminated by enzymatic treatment with α-galactosidases, as shown in the following reaction:

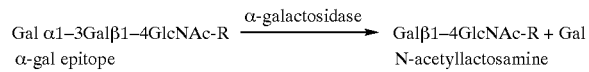

Gal α1–3Galβ1–4GlcNAc-R  →(α-galactosidase)→  Galβ1–4GlcNAc-R + Gal
α-gal epitope                                   N-acetyllactosamine The N-acetyllactosamine residues are epitopes that are normally expressed on human and mammalian cells and thus are not immunogenic. The in vitro digestion of the xenograft with glycosidases is accomplished by various methods. For example, the xenograft can be soaked or incubated in a buffer solution containing glycosidase. In addition, the xenograft can be pierced to increase permeability, as further described below. Alternatively, a buffer solution containing the glycosidase can be forced under pressure into the xenograft via a pulsatile lavage process.

Elimination of the α-gal epitopes from the xenograft diminishes the immune response against the xenograft. The α-gal epitope is expressed in nonprimate mammals and in New World monkeys (monkeys of South America) as $1\times10^6$–$35\times10^6$ epitopes per cell, as well as on macromolecules such as proteoglycans of the extracellular components. U. Galili et al., *Man, apes, and Old World monkeys differ from other mammals in the expression of α-galactosyl epitopes on nucleated cells*, 263 J. Biol. Chem. 17755 (1988). This epitope is absent in Old World primates (monkeys of Asia and Africa and apes) and humans, however. Id Anti-Gal is produced in humans and primates as a result of an immune response to α-gal epitope carbohydrate structures on gastrointestinal bacteria. U. Galili et al., *Interaction between human natural anti-α-galactosyl immunoglobulin G and bacteria of the human flora*, 56 Infect. Immun. 1730 (1988); R. M. Hamadeh et al., *Human natural anti-Gal IgG regulates alternative complement pathway activation on bacterial surfaces*, 89 J. Clin. Invest. 1223 (1992). Since nonprimate mammals produce α-gal epitopes, xenotransplantation of xenografts from these mammals into primates results in rejection because of primate anti-Gal binding to these epitopes on the xenograft. The binding results in the destruction of the xenograft by complement fixation and by antibody dependent cell cytotoxicity. U. Galili et al., *Interaction of the natural anti-Gal antibody with α-galactosyl epitopes: A major obstacle for xenotransplantation in humans*, 14 Immunology Today 480 (1993);

M. Sandrin et al., *Anti-pig IgM antibodies in human serum react predominantly with Galα1-3Gal epitopes*, 90 Proc. Natl. Acad. Sci. USA 11391 (1993); H. Good et al., *Identification of carbohydrate structures which bind human anti-porcine antibodies: implications for discordant grafting in man*. 24 Transplant. Proc. 559 (1992); B. H. Collins et al., *Cardiac xenografts between primate species provide evidence for the importance of the α-galactosyl determinant in hyperacute rejection*, 154 J. Immunol. 5500 (1995). Furthermore, xenotransplantation results in major activation of the immune system to produce increased amounts of high affinity anti-13 Gal. Accordingly, the substantial elimination of α-gal epitopes from cells and from extracellular components of the xenograft, and the prevention of reexpression of cellular α-gal epitopes can diminish the immune response against the xenograft associated with anti-Gal antibody binding with α-gal epitopes.

Further, the cartilage soft tissue xenografts of the present invention are particularly well suited to in vitro enzymatic elimination of the α-gal epitopes. In contrast to organs and other tissues, the cartilage extracellular matrix undergoes extremely slow turnover. Moreover, once the cartilage cells, i.e., the fibrochondrocytes are killed, these cells are prevented from reexpressing the α-gal epitopes, as discussed above.

In addition, the soft tissue xenografts may be treated with polyethylene glycol (PEG) prior to or concurrently with treatment with glycosidase. PEG acts as a carrier for the glycosidase by covalently bonding to the enzyme and to the collagen extracellular components. Further, PEG-treated xenografts have reduced immunogenicity.

Following treatment with glycosidase, the remaining carbohydrate chains (e.g., glycosaminoglycans) of the xenograft are optionally treated with capping molecules to cap at least a portion of the remaining carbohydrate chains. This capping treatment involves capping molecules having a concentration range of about 0.1 mM to about 100 mM, and preferably, a concentration of about 0.1 mM to about 10 mM, and most preferably, a concentration of about 1 mM to about 4 mM. Treatment with capping molecules is applicable to both glycosidase-treated and non-glycosidase-treated xenografts. For example, xenografts from knock out animals which may lack α-gal epitopes may be treated with capping molecules to cap carbohydrate moieties on the xenograft, thereby reducing the xenograft's immunogenicity. Examples of capping molecules used in the present invention include sialic acid, fucosyl and N-acetyl glucosamine.

In addition, selected capping molecules, such as sialic acid, are negatively charged. The replacement of α-gal epitopes with negatively charged molecules can further diminish immunogenic rejection of the xenograft. It is theorized that the decreased immunogenicity of the xenograft results because the negative charges conferred by the capping molecules repel negatively charged antibody molecules and/or cells of the immune system, thereby masking immunogenic regions of the xenograft.

In general, electrostatic repulsion termed "zeta potential," prevents the interaction between molecules, other than ligands and their corresponding receptors, in the body, and serves as a barrier against nonspecific interactions. For example, sialic acid on carbohydrate chains of envelope glycoproteins helps infectious viruses to evade effective recognition by antibodies and by antigen presenting cells. T. W. Rademacher et al., *Glycobiology*, Ann. Rev. Biochem., 57:785 (1988). Bacteria such as *Neisseria gonorrhea* can prevent their immune destruction by coating themselves with sialic acid using a bacterial sialyltransferase. R. F. Rest et al., *Neisseria sialyltransferases and their role in pathogenesis*, Microbial Pathogenesis, 19:379 (1995). Similarly, the protozoan *Trypanosoma cruzi* can infect humans and cause Chagas' disease because of effective sialylation of its cell surface glycoproteins with sialic acid by use of the enzyme transialidase which transfers sialic acid from host glycoproteins to carbohydrate chains on the parasite's membrane. O. Previato et al., *Incorporation of sialic acid into Trypanosoma cruzi macromolecules, A proposal for new metabolic route*, Mol. Biochem. Parasitol., 16:85 (1985); B. Zingales et al., *Direct sialic acid transfer from a protein donor to glycolipids of trypomastigote forms of Trypanosoma cruzi*, Mol. Biochem. Parasitol., 26:1335 (1987). Decreasing immunogenicity by sialic acid is a method also used by mammalian cells. Normal antigen presenting cells prevent nonspecific adhesion with T lymphocytes by the expression of a highly sialylated protein named sialophorin (also termed CD43). E. Famole-Belasio et al., *Antibodies against sialophorin (CD43) enhance the capacity of dendritic cells to cluster and activate T lymphocytes.*, J. Immunol., 159:2203 (1997). Many malignant cell types that acquire metastatic properties, increase the expression of sialic acid on their cell surface glycoproteins and thus mask their tumor antigens and decrease the possibility of their detection and destruction by the immune system. G. Yogeswarren et al., *Metastatic potential is positively correlated with cell surface sialylation of cultural murine cells*, Science, 212:1514 (1981); J. W. Dennis, *Changes in glycosylation associated with malignant transformation and tumor progression.* In: Cell surface carbohydrates and cell development M. Fukuda, Ed. CRC Press, pp. 161–213 (1992).

The same strategy for prevention of immune recognition can be implemented by treatment of α-galactosidase treated xenografts with negatively charged molecules. Many of the antigens within a xenograft are effectively masked from the host immune system by the high density of carbohydrate chains. Most of these chains are negatively charged and are the same in the various mammalian species. D. Heinegard et al., *Structure and biology of cartilage and bone matrix noncolagenous macromolecules*, FASEB J., 3:2042 (1989); U. Lindahl et al., *Glycosaminoglycans and their binding to biological macromolecules*, Ann. Rev., Biochem, 47:385 (1978). Other antigens, however, are not masked by densely concentrated carbohydrate chains and thus may elicit an immune response against the xenograft. For example, some peptide regions, primarily in the proteoglycans of the extracellular components, are not masked by densely concentrated carbohydrate chains of keratan sulfate and chondroitin sulfate, and may elicit an immune response against the xenograft. The addition of negatively charged molecules to the ends of the carbohydrate chains on the cells and/or on the extracellular molecules of the α-galactosidase treated xenografts can mask the non-α-Gal antigens of the xenograft and diminish immunogenic rejection of the xenograft.

Sialic acid is a non-limiting example of a negatively charged capping molecule used to cap the carbohydrate chains of the xenograft of the present invention. Sialic acid can be linked in vitro to carbohydrate chains of the xenograft by sialyltransferase (ST), preferably in a concentration of about 1 mU/ml to about 1000 U/ml, and more preferably in a concentration of about 10 U/ml to about 200 U/ml, in the following exemplary reaction:

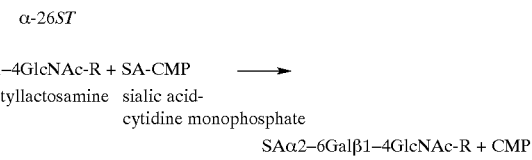

Sialic acid can also be linked in vitro to carbohydrate chains of the xenograft by recombinant trans-sialidase (TS), preferably in a concentration of about 1 mU/ml to about 1000 U/ml, and more preferably in a concentration of about 10 U/ml to about 200 U/ml, in the following exemplary reaction:

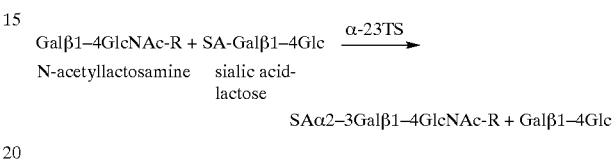

Prior to treatment, the outer surface of the xenograft (e.g., the outer lateral surface of meniscus soft tissue xenografts) optionally may be pierced to increase permeability to agents used to render the xenograft substantially non-immunogenic. A sterile surgical needle such as an 18 gauge needle may be used to perform this piercing step, or, alternatively a comb-like apparatus containing a plurality of needles may be used. The piercing may be performed with various patterns, and with various pierce-to-pierce spacings, in order to establish a desired access to the interior of the xenograft. Piercing may also be performed with a laser. In one form of the invention, one or more straight lines of punctures about three millimeters apart are established circumferentially in the outer lateral surface of the xenograft.

Prior to implantation, the soft tissue xenograft of the invention may be treated with limited digestion by proteolytic enzymes such as ficin or trypsin to increase tissue flexibility, or coated with anticalcification agents, antithrombotic coatings, antibiotics, growth factors, or other drugs which may enhance the incorporation of the xenograft into the recipient joint. The soft tissue xenograft of the invention may be further sterilized using known methods, for example, with additional glutaraldehyde or formaldehyde treatment, ethylene oxide sterilization, propylene oxide sterilization, or the like. The xenograft may be stored frozen until required for use.

The soft tissue xenograft of the invention, or a segment thereof, may be implanted into damaged human joints by those of skill in the art using known arthroscopic surgical techniques. Specific instruments for performing arthroscopic techniques are known to those of skill in the art, which ensure accurate and reproducible placement of soft tissue implants. *Meniscus Cartilage Soft Tissue Xenograft Implantation*

For meniscal cartilage replacement to succeed, the following goals are preferably accomplished:

1. The torn fragmented pieces of native meniscal cartilage must be removed.
2. The attachment sites for the meniscal horns must be anatomically placed.
3. The periphery of the meniscal implant must be attached securely enough to permit axial and rotational loads.
4. The surrounding capsule and ligaments of the knee joint must be neither excessively violated nor constrained by the fixation technique. The method of meniscal implantation described in detail below is derived from K. R. Stone, et al., *Arthroscopy: The Journal of Arthroscopic and Related Surgery* 9, 234–237 (1993); other methods of meniscal implantation may also be employed to use the xenogeneic meniscal xenografts of the present invention.

Figure 3:
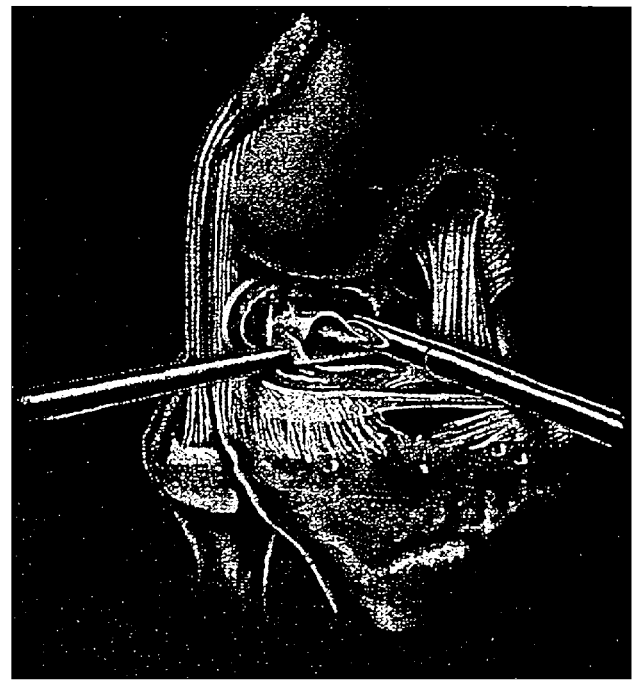
FIG. 3 is a diagrammatic representation of resection of a torn lateral meniscus of a human knee, and preparation of the knee for receipt of a meniscal implant.

Initially, complete diagnostic arthroscopy of the knee joint is accomplished using known methods. If ACL surgery is to be performed simultaneously, the femoral and tibial tunnels for the cruciate reconstruction should be drilled first. The torn portion of the meniscal cartilage is evaluated. If meniscal repair cannot be accomplished due to severity of the tear or poor quality of the tissue, then preparation of the meniscal rim is undertaken by removing the torn portions of the cartilaginous tissue (FIG. 3). When the entire human meniscus is to be replaced by a xenogeneic meniscus xenograft of the invention, nearly all of the human meniscus is removed. Additionally, for replacement of the entire human meniscus with a xenogeneic meniscus xenograft of the invention, resection of the human meniscal horns and preparation of bony tunnels to accept bone plugs may be required. When only a portion of the human meniscus is to be replaced with a segment of the xenogeneic meniscus xenograft of the invention, only the damaged portions are removed, preserving the peripheral rim and horns for attachment of the xenogeneic meniscus xenograft segment. If absolutely no human meniscal rim is present, then partial replacement of the meniscus should not be performed. If the joint is excessively tight, a joint distractor may be applied or the medial collateral ligament may be partially released.

Figure 4:
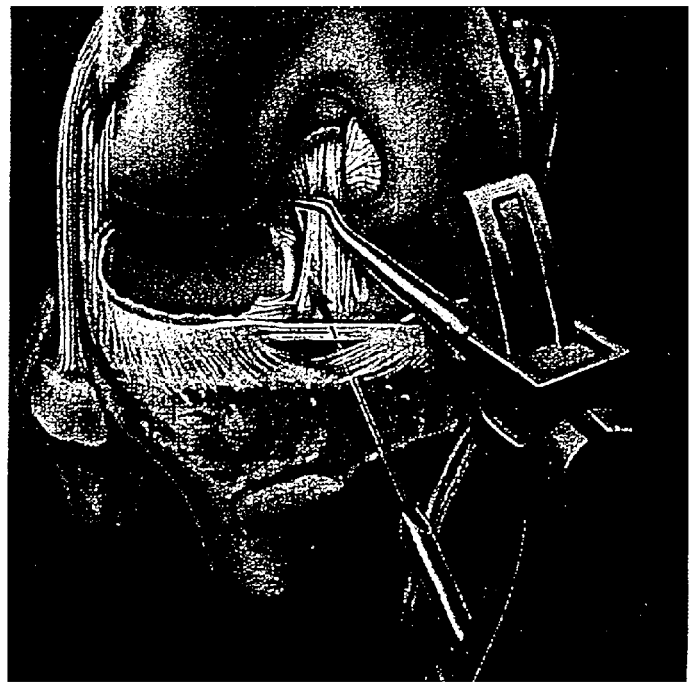
FIG. 4 is a diagrammatic representation the preferred drill guide placement for posterior lateral meniscal horn insertion into a human knee.
Figure 5:
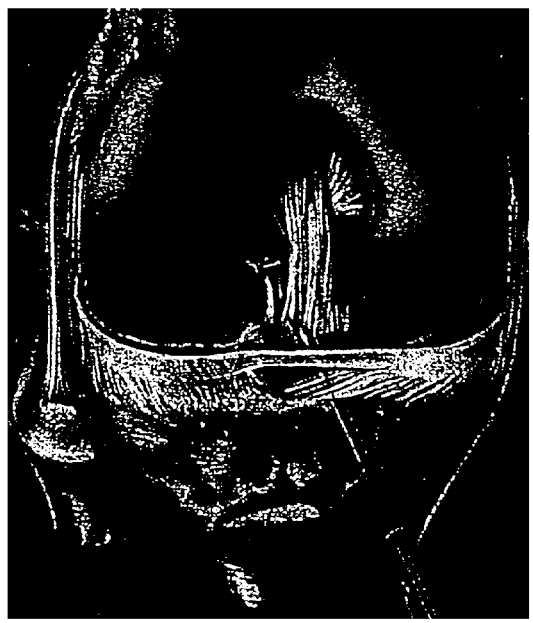
FIG. 5 is a diagrammatic representation of a cannulated drill overdrilling guide wire at the posterior lateral meniscal horn insertion into a human knee.

For medial or lateral meniscal replacement, the arthroscope is placed in the mid-lateral or anterior lateral portal and the tibial guide is placed through the anterior medial portal. The tip of the guide is brought first to the posterior horn of the meniscus. It should be noted that the posteromedial horn inserts on the posterior slope of the tibial eminence. A drill pin is then brought from the anterior medial side of the tibial tuberosity to the posterior horn insertion (FIG. 4). The pin placement can be confirmed by passing the arthroscope through the intercondylar notch and viewing the exit site of the pin. Extreme care must be undertaken to avoid penetration through the posterior capsule of the knee, endangering the neurovascular bundle. When the pin position is confirmed, the pin is then overdrilled with a 4.5-mm cannulated drill bit with the option of a drill stop to prevent posterior capsular penetration (FIG. 5). The bit is left in place and used as a tunnel for passage of a suture passer with a suture such as a #2 Ethibond™ suture available from Johnson & Johnson. The suture is passed up the bore of the drill bit, the drill bit removed, and the suture left in place.

Figure 6:
FIG. 6 is a diagrammatic representation of the appearance of a human knee with posterior and anterior drill holes for meniscal horn insertion.

The anterior medial meniscus insertion point in humans varies considerably, most often being found anterior to the medial tibial eminence. The anterior horn of the lateral meniscus inserts just posterior to the anterior cruciate ligament. An anterior drill hole is made by first identifying the insertion point of the anterior horn of the lateral meniscus, by placing the tip of the drill guide so that a relatively vertical hole will be made (FIG. 6). The drill pin is placed, then the cannulated drill bit is used to overdrill the drill pin placement to form the anterior drill hole. A suture passer is placed in the anterior drill hole. Alternatively, the anterior horn of the medial meniscus is affixed with a suture anchor directly to bone as opposed to a drill hole.

Before the suture is grasped from the anterior and posterior drill holes, the anterior portal is widened to approximately 2 cm. The suture grasper is then passed through the widened portal, and both the anterior and the posterior sutures brought out simultaneously. This technique prevents the sutures from becoming entangled in two different planes of the fat pad and capsular tissue.

Figure 7:
FIG. 7 is a diagrammatic representation of the preferred suture passer placement for pulling a meniscal implant into a human knee joint.
Figure 8:
FIG. 8 is a diagrammatic representation of the appearance of a human knee containing a meniscal implant during the insertion stage.

The implant is now brought onto the field. Two horizontal mattress sutures, for example, #2-0 Ethibond™ sutures or the like, are placed through each horn of the xenogeneic meniscus xenograft with the free ends exiting the inferior surface (FIG. 7). The two posterior sutures are then drawn through the knee and out the posterior tibial tunnel (FIG. 8). If viewing from a mid-lateral portal, the anterolateral portal can be used for probe insertion to push the implant medially into place through a 1-inch incision. No insertion cannula is required. The anterior sutures are then similarly passed. The horn sutures are then tied over the anterior tibial bony bridge.

Figure 9:
FIG. 9 is a diagrammatic representation of the appearance of a human knee containing a meniscal implant with zone-specific meniscal repair sutures in place for final tying of the meniscal repair sutures.
Figure 10:
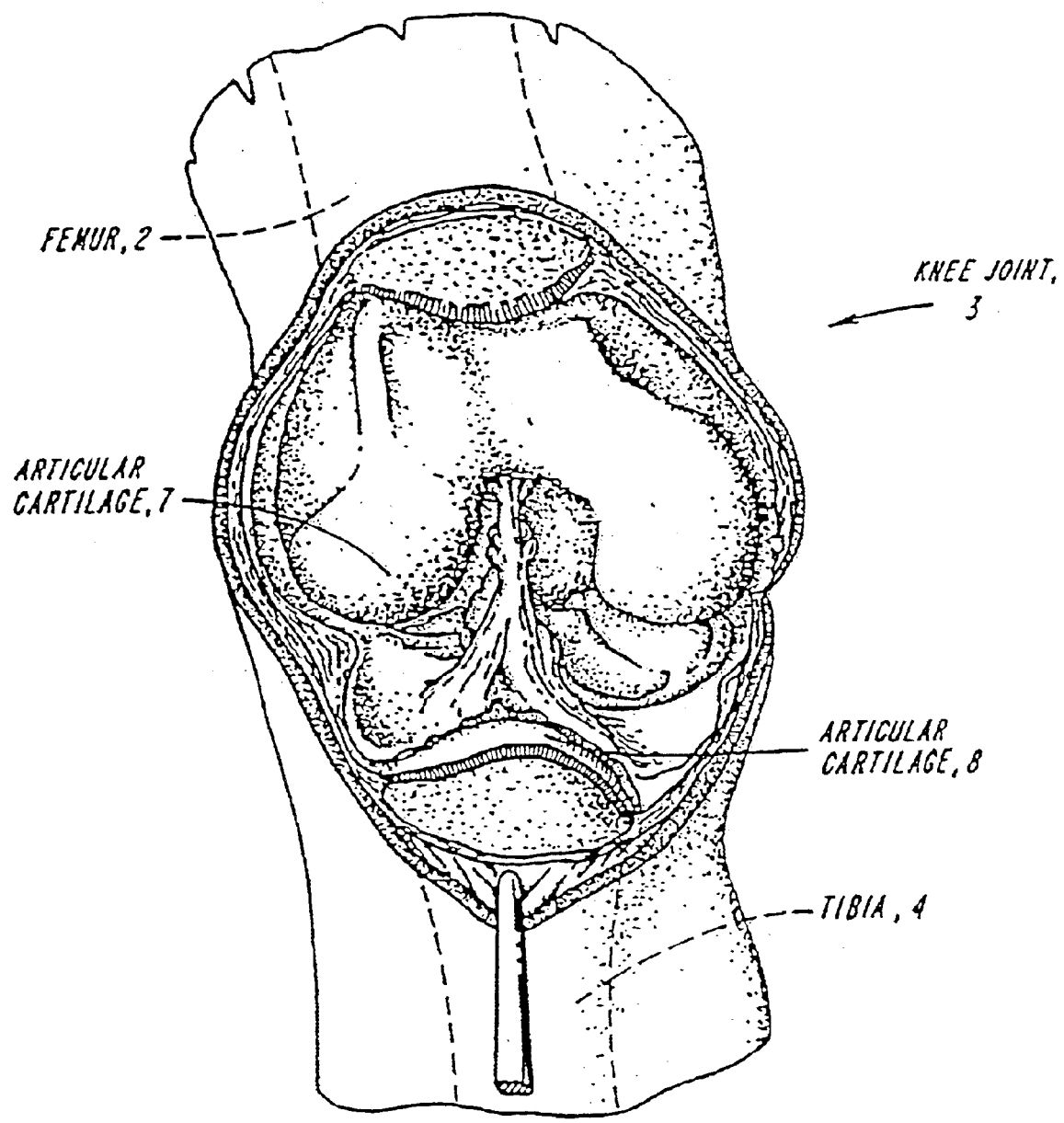
FIG. 10 is shows a simplified diagrammatic representation of a human knee joint 3, showing the normal positioning of articular cartilage 7 on the articulating end of femur 2 and articular cartilage 8 on the articulating end of tibia 4.

Next, zone specific meniscal repair cannulae are brought into place. For medial insertions, a posterior medial vertical incision is made one third of the distance from the back of the knee for protection of the saphenous nerve and for retrieval of the inside-out meniscal repair needles. A second vertical incision is usually required further anteriorly, next to the anterior medial arthroscopy portal, to capture the anterior exiting needles. Through these two incisions, the suture needles can be captured and the knots placed directly over the capsule (FIG. 9).

When using the meniscal repair needles, the posterior cannulae should be used first, with the sutures placed vertically and evenly spaced. The repair should proceed from posterior to anterior so that a buckle is not produced within the xenograft. Each knot is tied as it is placed to avoid the chance of suture tangling. The knots are spaced approximately 4 mm apart. The knee is cycled through several complete ranges of motion of ensure that the xenograft moves smoothly without impingement.

When performing a lateral meniscal replacement, the medial portal is suitable for xenograft insertion. This may require excision of the ligamentous mucosa and removal of a portion of the fat pad. The drill guide for the posterior horn of the lateral meniscus is inserted through the anteromedial portal. The posterior slope of the lateral tibial spine must be identified for accurate meniscal horn insertion. The anterior horn inserts on the anterior slope of the lateral tibial spine in approximation to the lateral aspect of the anterior cruciate ligament. The advantage of drilling these holes from the medial side is that the tunnel divergence will be greater, providing a larger bony bridge between the horn insertions. The remainder of the insertion technique remains the same, except that great care should be taken to protect the neurovascular bundle when suturing the posterior horn. Accessing posterolateral exposure is necessary to safeguard the common peroneal nerve and to expose the lateral capsule. If there is any doubt about the suture placement, open posterior horn suturing should be performed in the standard fashion. Alternatively, meniscus and/or stabilization devices such as arrows or staples can be used instead of sutures. Stabilization arrows manufactured by Bionix, Inc., Malvern, Pa., are non-limiting examples of such stabilization arrows. Other stabilization devices known to those of ordinary skill in the art can also be used.

Routine skin closure and dressings are applied. Thirty milliliters of 0.5% Marcaine (Astra) with epinephrine may be instilled if desired. A postoperative hinged knee brace is applied with the range of motion limited to 30° of extension and 90° of flexion.

Postoperatively the patient is permitted partial weight bearing in a hinged knee brace for six weeks. The brace is removed for sleeping and out-of-brace range-of-motion exercises. On day one after surgery, exercises are initiated for quad strengthening, including leg raises, quad sets, and well-leg bicycling. After six weeks, knee-bend exercises, two-leg bicycling, and water running exercises are initiated. When maximal strength gains are achieved, pivoting sports can be resumed, usually at four to six months after surgery.

Articular Cartilage Soft Tissue Xenograft Implantation

The underlying bone bed of the recipient joint is prepared with a bone burr to produce a cancellous bleeding bed. Grafting can involve either the entire articular surface or a portion of the articular surface. The substantially non-immunogenic articular cartilage xenograft of the invention is applied to the recipient joint as a cover, which is held in place by one or more suture anchors, absorbable pins, screws, staples, and the like. A fibrin clot may also be used to hold the substantially non-immunogenic articular cartilage xenograft in place.

Ligament Soft Tissue Xenograft Implantation

The irreparably damaged ligament is removed with a surgical shaver. The anatomic insertion sites for the ligament are identified and drilled to accommodate a bone plug. The size of the bone plug can be about 9–10 mm in width by about 9–10 mm in depth by about 20–40 mm in length. The xenogeneic ligament is brought through the drill holes and affixed with interference screws. Routine closure is performed.

This invention is further illustrated by the following Examples which should not be construed as limiting. The contents of all references and published patents and patent applications cited throughout the application are hereby incorporated by reference.

EXAMPLE 1

Assay for α-Gal Epitopes' Elimination From Soft Tissue by α-Galactosidase

In this example, an ELISA assay for assessing the elimination of α-gal epitopes from soft tissue is conducted.

A monoclonal anti-Gal antibody (designated M86) which is highly specific for α-gal epitopes on glycoproteins is produced by fusion of splenocytes from anti-Gal producing knock-out mice for α 1,3 galactosyltransferase, and a mouse hybridoma fusion partner.

Figure 11:
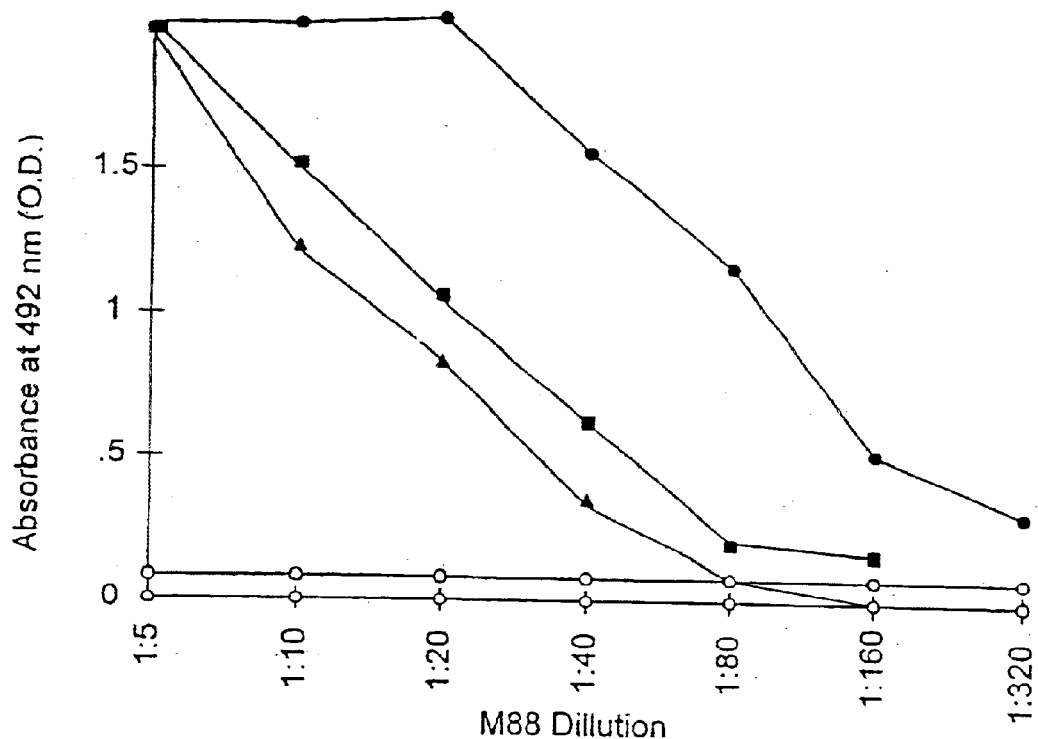
FIG. 11 is a graphical representation of the specificity of monoclonal anti-Gal antibodies for α-galactosyl epitopes on bovine serum albumin (BSA), bovine thyroglobulin, mouse laminin, Galβ1-4 GlcNAc-BSA (N-acetyllactosamine-BSA), Galα1-4Galβ1-4G1cNAc-BSA (P1 antigen linked to BSA), and human thyroglobulin or human laminin.

The specificity of M86 for α-gal epitopes on glycoproteins is illustrated in FIG. 11. M86 binds to synthetic α-gal epitopes linked to ●-bovine serum albumin (BSA), to ▼-bovine thyroglobulin which has 11 α-gal epitopes, R. G. Spiro et al., *Occurrence of α-D-galactosyl residues in the thyroglobulin from several species. Localization in the saccharide chains of complex carbohydrates*, 259 J. Biol. Chem. 9858 (1984); or to ▮-mouse laminin which has 50 α-gal epitopes, R. G. Arumugham et al., *Structure of the asparagine-linked sugar chains of laminin*. 883 Biochem. Biophys. Acta 112 (1986); but not to ☐-human thyroglobulin or human laminin, ○-Galβ1-4 GlcNAc-BSA (N-acetyllactosamine-BSA) and Galα1-4Galβ1-4GlcNAc-BSA (P1 antigen linked to BSA), all of which completely lack α-gal epitopes. Binding is measured at different dilutions of the M86 tissue culture medium.

Once the M86 antibody is isolated, the monoclonal antibody is diluted from about 1:20 to about 1:160, and preferably diluted from about 1:50 to about 1:130. The antibody is incubated for a predetermined period of time ranging between about 5 hr to about 24 hr, at a predetermined temperature ranging from about 3° C. to about 8° C. The antibody is maintained in constant rotation with fragments of soft tissue about 5 μm to about 100 μm in size, and more preferably with soft tissue fragments ranging from about 10 μm to about 50 μm in size, at various soft tissue concentrations ranging from about 200 mg/ml to about 1.5 mg/ml. Subsequently, the soft tissue fragments are removed by centrifugation at centrifugation rate ranging from about 20,000×g to about 50,000×g. The proportion of M86 bound to the soft tissue is assessed by measuring the remaining M86 activity in the supernatant, in ELISA with α-gal-BSA as described in the prior art in, for example, U. Galili et al., *Porcine and bovine cartilage transplants in cynomolgus monkey: II. Changes in anti-Gal response during chronic rejection*, 63 Transplantation 645–651 (1997). The extent of binding of M86 to the soft tissue is defined as a percentage inhibition of subsequent binding to α-gal-BSA. There is a direct relationship between the amount of α-gal epitopes in the soft tissue and the proportion of M86 complexed with the soft tissue fragments, thus removed from the supernatant (i.e., percentage inhibition).

Figure 12:
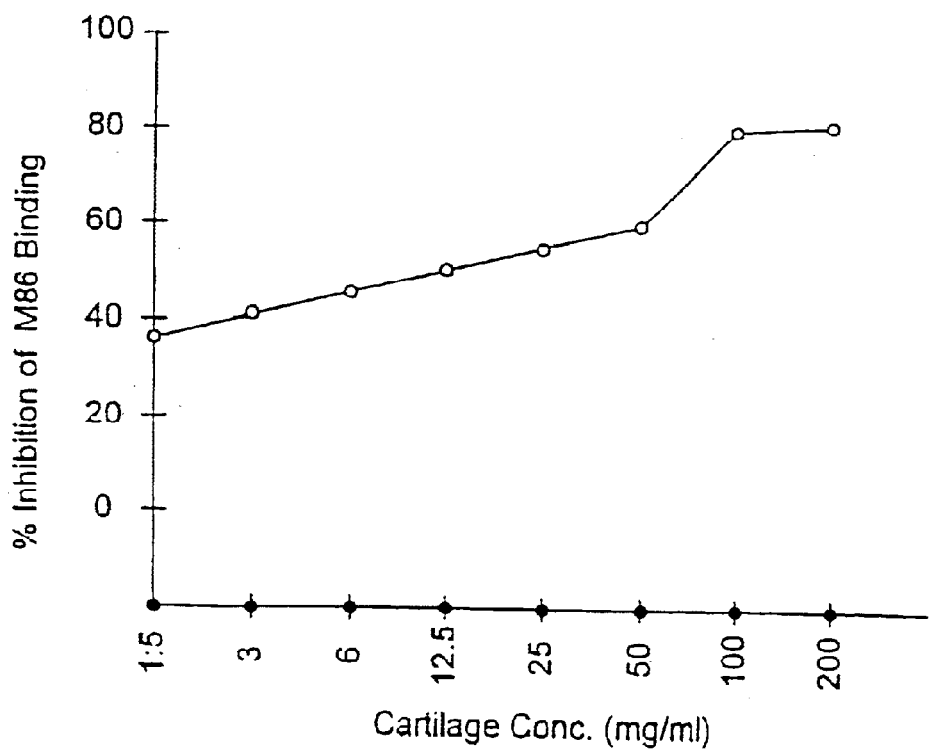
FIG. 12 is a graphical representation of α-galactosyl epitope elimination from α-galactosidase treated meniscal cartilage.

An example of the assay is shown in FIG. 12. Fragments of homogenized meniscus cartilage (○) or meniscus cartilage (●) treated with α-galactosidase are incubated with the M86 monoclonal antibody (diluted 1:100) for 20 hr at 4° C. Subsequently, the meniscus cartilage fragments are removed by centrifugation at 35,000×g and the remaining M86 in the supernatant is assessed in ELISA with α-gal-BSA as solid phase antigen. FIG. 12 shows that treatment of the meniscus cartilage with 200 U/ml α-galactosidase for 4 hour at 30° C. followed by five washes with phosphate-buffered solution (PBS) completely eliminates the α-gal epitopes. Thus, since there is no inhibition of subsequent M86 binding to α-gal-BSA even at a high meniscus cartilage fragment concentration of 200 mg/ml.

EXAMPLE 2

Assessment of Primate Response to Implanted Porcine Meniscus Cartilage Soft Tissue Treated With α-Galactosidase In this example, porcine meniscus and articular cartilage, and bovine ligament soft tissue implants are treated with α-galactosidase to eliminate α-galactosyl epitopes, the implants are transplanted into cynomolgus monkeys, and the primate response to the soft tissue implants is assessed.

Porcine stifle joints are sterilely prepared and meniscus cartilage and articular cartilage and other surrounding attached soft tissues surgically removed. The meniscus cartilage and the articular cartilage soft tissue specimens are washed for at least five minutes with an alcohol, such as ethanol or isopropanol, to remove synovial fluid and lipid soluble contaminants. The meniscus cartilage and the articular cartilage soft tissue specimens are frozen at a temperature ranging from about −35° C. to about −90° C., and preferably at a temperature up to about −70° C., to disrupt, that, is to kill, the specimens' fibrochondrocytes.

Bovine stifle joints are also sterilely prepared and ligaments, each with a block of bone attached to one or both ends, are removed in the cold, under strict sterile technique. Each of the blocks of bone represents a substantially cylindrical plug of approximately 9 mm in diameter by about 40 mm in length. Each ligament soft tissue specimen is carefully identified and dissected free of adhering tissue, thereby forming the xenograft. The ligament soft tissue xenograft specimens are then washed for at least five minutes with an alcohol, such as ethanol or isopropanol, to remove synovial fluid and lipid soluble contaminants. Subsequently, the specimens are frozen at a temperature of about −70° C. to disrupt, that is, to kill, the ligament specimens' cells.

Each meniscus cartilage, articular cartilage and ligament soft tissue xenograft specimen is cut into two portions. Each first portion is immersed in a buffer solution containing α-galactosidase at a predetermined concentration. The specimens are allowed to incubate in the buffer solutions for a predetermined time period at a predetermined temperature. Each second portion is incubated under similar conditions as the corresponding first portion in a buffer solution in the absence of α-galactosidase and serves as the control.

At the end of the incubation, the soft tissue xenograft specimens are washed under conditions which allow the enzyme to diffuse out. Assays are performed to confirm the complete removal of the α-gal epitopes.

Each meniscus cartilage soft tissue xenograft specimen is implanted in the supra patellar pouch of six cynomolgus monkeys. With the animals under general inhalation anesthesia, an incision of about 1 cm is made directly into the supra patellar pouch at the superior medial border of the patella extending proximally. A piece of the porcine cartilage soft tissue of about 0.5 cm to about 1 cm in length is placed into the pouch with a single 3-0 nylon stitch as a marking tag.

The articular cartilage xenograft specimens are implanted in the supra patellar pouch of six cynomolgus monkeys substantially following the above-identified implantation procedure.

The ligament soft tissue xenograft specimens are implanted in six cynomolgus monkeys using the following implantation procedure. With the animals under general inhalation anesthesia, the anatomic insertion sites for the xenogeneic ligament are identified and drilled to accommodate a substantially 9 mm in diameter by 40 mm in length bone plug. The xenogeneic ligament is brought through the drill holes and affixed with interference screws.

The implantation procedures are performed under sterile surgical technique, and the wounds are closed with 3-0 vicryl or a suitable equivalent known to those of ordinary skill in the art. The animals are permitted unrestricted cage activity and monitored for any sign of discomfort, swelling, infection, or rejection. Blood samples (e.g., 2 ml) are drawn periodically (e.g., every two weeks) for monitoring of antibodies.

The occurrence of an immune response against the xenograft is assessed by determining anti-Gal and non-anti-Gal anti-soft tissue antibodies (i e., antibodies binding to soft tissue antigens other than the α-gal epitopes) in serum samples from the transplanted monkeys. At least two ml blood samples are drawn from the transplanted monkeys on the day of implant surgery and at periodic (e.g., two week) intervals post-transplantation. The blood samples are centrifuged and the serum samples are frozen and evaluated for the anti-Gal and other non-anti-Gal anti-soft tissue antibody activity.

Anti-Gal activity is determined in the serum samples in ELISA with α-gal-BSA as solid phase antigen, according to methods known in the prior art, such as, for example, the methods described in Galili et al., *Porcine and bovine cartilage transplants in cynomolgus monkey: II. Changes in anti-Gal response during chronic rejection*, 63 Transplantation 645–651 (1997).

Assays are conducted to determine whether α-galactosidase treated xenografts induce the formation of anti-soft tissue antibodies. For measuring anti-soft tissue antibody activity, ELISA assays are performed according to methods known in the prior art, such as, for example, the methods described in K. R. Stone et al., *Porcine and bovine cartilage transplants in cynomolgus monkey: I. A model for chronic xenograft rejection*, 63 Transplantation 640–645 (1997).

The soft tissue xenograft specimens are optionally explanted at one to two months post-transplantation, sectioned and stained for histological evaluation of inflammatory infiltrates. Post-transplantation changes in anti-Gal and other anti-cartilage soft tissue antibody activities are correlated with the inflammatory histologic characteristics (i.e., granulocytes or mononuclear cell infiltrates) within the explanted soft tissue, one to two months post-transplantation, using methods known in the art, as, for example, the methods described in K. R. Stone et al., *Porcine and bovine cartilage transplants in cynomolgus monkey: I. A model for chronic xenograft rejection*, 63 Transplantation 640–645 (1997).

Where the soft tissue is explanted, the soft tissue xenografts are aseptically harvested, using anesthetic procedure, surgical exposure of joints, removal of the implants and closure of the soft tissue (where the animals are allowed to recover). At the time of the xenograft removal, joint fluid, if present in amounts sufficient to aspirate, is collected from the stifle joints for possible immunologic testing if the gross and histopathologic evaluation of the transplants indicate good performance of the transplanted soft tissue.

The animals which have had meniscus cartilage or articular cartilage xenograft implantations are allowed to recover and are monitored closely until the incisions have healed and the gait is normal. The xenograft samples are collected, processed, and examined microscopically.

Portions of the meniscus cartilage, articular cartilage and ligament implants and surrounding tissues are frozen in embedding mediums for frozen tissue specimens in embedding molds for immunohistochemistry evaluation according to the methods known in the prior art. "TISSUE-TEK®" O.C.T. compound which includes about 10% w/w polyvinyl alcohol, about 4% w/w polyethylene glycol, and about 86% w/w nonreactive ingredients, and is manufactured by Sakura FinTek, Torrence, Calif., is a non-limiting example of a possible embedding medium for use with the present invention. Other embedding mediums known to those of ordinary skill in the art may also be used. The remaining implant and surrounding tissue is collected in 10% neutral buffered formalin for histopathologic examination.

EXAMPLE 3

Assessment of Primate Response to Implanted Meniscus Cartilage, Articular Cartilage and Ligament Soft Tissue Treated With α-Galactosidase, Fucosyl and Fucosyltransferase In this example, porcine meniscus cartilage and articular cartilage soft tissue implants, and bovine ligament soft tissue implants are treated with α-galactosidase to eliminate α-gal epitopes, as described in Example 1. The soft tissue implants are further treated with fucosyl and fucosyl transferase to cap remaining carbohydrate chains with fucosyl. Fucosyltransferase facilitates the transfer of fucosyl to the xenograft. The fucosyl links to and thus caps the remaining carbohydrate chains. Capping with fucosyl interferes with the ability of the subject's immune system to recognize the xenograft as foreign. The soft tissue implants are transplanted into cynomolgus monkeys, and the primate response to the soft tissue implants is assessed.

Meniscus cartilage and articular cartilage implants from porcine stifle joints and ligament implants from bovine stifle joints are prepared as the implants were prepared in Example 1 including the α-galactosidase treatment. Prior to implantation into the monkeys, however, the implants are further treated with a predetermined amount of fucosyl and fucosyltransferase, at specified concentrations for a predetermined time and at a predetermined temperature, to cap remaining carbohydrate chains with flicosyl. For example, the implants are immersed in buffer solutions at predetermined concentrations of fucosyl and fucosyl transferase. The implants are incubated for a predetermined time period at a predetermined temperature.

Other molecules, such as N-acetyl glucosamine in combination with the corresponding glycosyltransferase, can also be used for capping the carbohydrate chains of the implants.

Subsequently, the implants are washed to remove the enzyme and implanted into the monkeys, and the occurrence of an immune response against the xenograft is assessed as described above in Example 1.

EXAMPLE 4

Assessment of Capping With Sialic Acid of Carbohydrate Moieties on α-Galactosidase Treated Porcine Articular Cartilage Using Sialyltransferase and Trans-sialidase In this example, α-galactosidase treated porcine articular cartilage is treated with sialic acid using α-26 sialyltransferase (ST) or α-23 trans-sialidase (TS) to confirm the ability to cap the carbohydrate moieties of the cartilage with sialic acid.

Figure 13A:
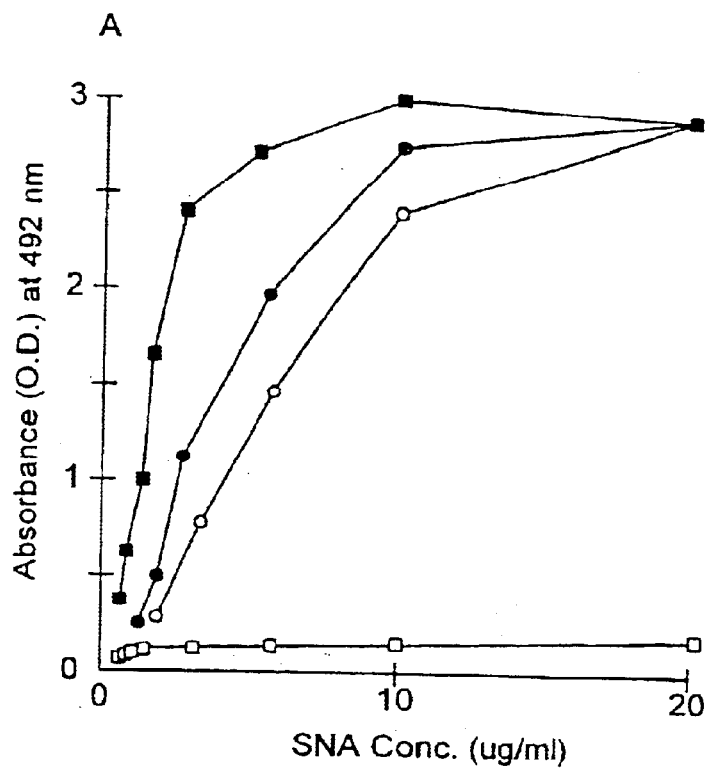
FIG. 13A is a graphical representation of the capping with sialic acid of carbohydrate moieties on α-galactosidase treated articular cartilage using sialyltransferase to form SAα2-6Galβ1-4GlcNAc-R residues on the ends of cartilage carbohydrate chains, as measured by the binding of Sambucus nigra lectin to the residues.

Articular cartilage treated with α-galactosidase is attached as homogenate to ELISA wells by drying 5 μg cartilage homogenate per well. In selected wells, after blocking with bovine serum albumin, 10 U/ml of α-26 ST (manufactured by Calbiochem, San Diego, Calif.) and 2 mM of sugar donor cytidine monophosphate-sialic acid (CMP-SA) (manufactured by Sigma, Inc., St. Louis, Mo.) are added to the wells. The lectin Sambucus nigra lectin (SNA) (manufactured by Vector Labs, Burlingame, Calif.) which is specific for the Saα2-6Galβ1-4GlcNAc-R epitope, is then added to the wells at concentrations of up to 20 μg/ml. The degree of binding of the SNA lectin to the Saα2-6Galβ1-4GlcNAc-R epitope is measured in the wells containing the sialylated α-galactosidase-treated cartilage and in the wells containing α-galactosidase-treated cartilage without sialylation. Binding of the SNA lectin to sialylated and de-sialylated fetuin (manufactured by Sigma, Inc., St. Louis, Mo.) is also measured to compare sialic acid capping in α-galactosidase treated cartilage with sialic acid capping in known molecules. FIG. 13A shows the binding of the SNA lectin to α-galactosidase treated cartilage without sialylation (○), to sialylated α-galactosidase treated cartilage (●), to desialylated fetuin (□), and to sialylated fetuin (■).

As shown in FIG. 13A, the α-galactosidase treated cartilage without sialylation displays a basal level of binding of the lectin to the cartilage. This binding occurs because the lectin binds to the naturally produced Saα2-6Galβ1-4GlcNAc-R epitopes on some of the carbohydrate chains of the cartilage. After treatment with α-26 ST, there is a significant increase in the binding of the SNA lectin to the cartilage, however, because of the de novo synthesis of Saα2-6Galβ4GlcNAc-R epitopes on the carbohydrate chains of the cartilage following the capping with sialic acid.

Figure 13B:
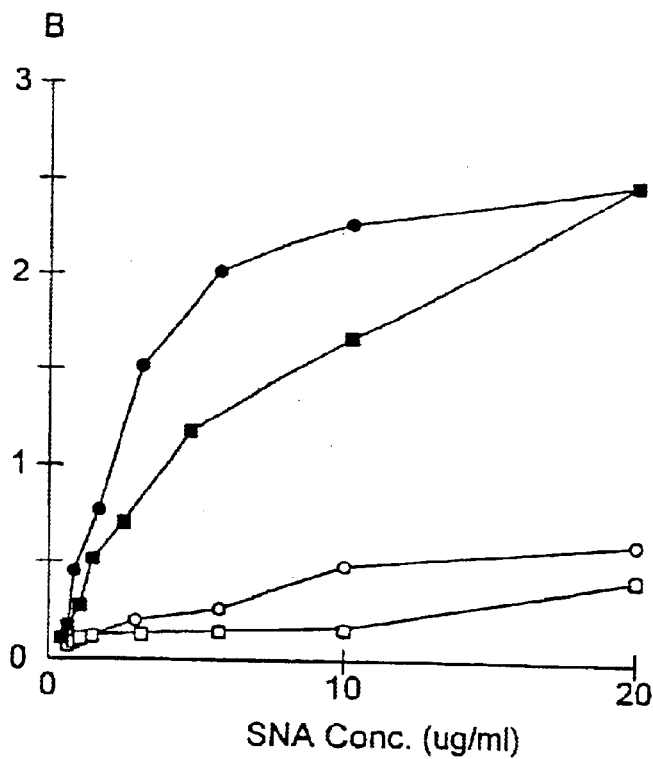
FIG. 13B is a graphical representation of the capping with sialic acid of carbohydrate moieties on α-galactosidase treated articular cartilage using trans-sialidase to form Saα2-3Galβ1-4GlcNAc-R residues on the ends of cartilage carbohydrate chains, as measured by the binding of Maackia amurensis lectin II to the residues.

The above procedure is repeated substituting α-23 TS (manufactured by Neos Technologies, Inc., Horsham, Pennsylvania) for α-26 ST; the sugar donor sialic acid-lactose (SA-Gaβ1-4Glc) (manufactured by Neos Technologies, Inc., Horshan, Pa.), for CMP-SA; and the lectin Maackia amurensis lectin II (MALII) (manufactured by Vecor Labs, Burlingame, Calif.) which is specific for the Saα2-3Galβ1-4GlcNAc-R epitope, for SNA. The degree of binding of the MAL II lectin to the Saα2-3Galβ1-4GlcNAc-R epitope in α-galactosidase treated cartilage with and without sialylation is measured along with the binding of the MAL II lectin to sialylated and de-sialylated fetuin. FIG. 13B shows the binding of the MAL II lectin to α-galactosidase treated cartilage without sialylation (○), to sialylated α-galactosidase treated cartilage (●), to desialylated fetuin (□), and to sialylated fetuin (■).

As shown in FIG. 13B, and similar to FIG. 13A, the α-galactosidase treated cartilage without sialylation displays a basal level of binding of the MAL II lectin, where the lectin binds to the naturally produced SAα2–3Galβ1-4GlcNAc-R epitopes on some of the carbohydrate chains of the cartilage. After treatment with α-23 TS, there is a significant increase in the binding of the MAL II lectin to the cartilage, however, because of the de novo synthesis of Saα2–3Galβ1-4GlcNAc-R epitopes on the carbohydrate chains of the cartilage as a result of the sialic acid capping.

Those of skill in the art will recognize that the invention may be embodied in other specific forms without departing from the spirit or essential characteristics thereof The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. A method of preparing a soft tissue xenograft for implantation into a human, which comprises:

a. removing at least a portion of a soft tissue from a non-human animal to provide a xenograft, b. washing the xenograft in water and alcohol;

c. subjecting the xenograft to a cellular disruption treatment; and d. treating the xenograft with a glycosidase to remove a plurality of first surface carbohydrate moieties, whereby the xenograft has substantially the same mechanical properties as a corresponding portion of a native soft tissue, where the glycosidase has a concentration in a range of about 1 mU/ml to about 1000 U/ml;

wherein (i) the cellular disruption treatment comprises freeze/thaw cycling or exposure to gamma radiation; and (ii) further comprises the steps of:

a) prior to step c, piercing the xenograft;

b) following step c, treating the xenograft with a second enzyme;

c) following step c, treating the xenograft with one or more agents selected from the group consisting of anticalcification agents, antithrombotic agents, antibiotics, and growth factors;

d) following step c, sterilizing the xenograft;

e) following step c, treating the xenograft with polyethylene glycol;

f) following step d, treating a plurality of second surface carbohydrate moieties on the xenograft with a plurality of capping molecules to cap at least a portion of the second surface carbohydrate moieties, whereby the xenograft is substantially non-immunogenic; and g) following step c, exposing the xenograft to a crosslinking agent in a vapor form.

2. The method of claim 1, wherein the soft tissue is selected from the group consisting of:

a) a medial or lateral meniscus from a knee joint, and optionally the removing step comprises removing the medial or lateral meniscus having a superior principal surface and an inferior principal surface, the outer portions of the principal surfaces being joined by an outer lateral surface, and the inner portions of the principal surfaces being joined by an inner lateral surface;

b) a ligament or tendon, and optionally the removing step comprises removing with the portion a first block of bone attached to a first end of the portion, and further optionally the removing step comprises removing with the portion a second block of bone attached to a second end of the portion opposite the first end;

c) an articular cartilage, and optionally the removing step comprises removing with the portion a layer of subchondral bone; and d) a combination thereof.

3. An article of manufacture comprising a substantially non-immunogenic soft tissue xenograft for implantation into a human, produced by the method of any one of claims 1 and 2.

4. The method of claim 1, wherein the capping step comprises treating the second surface carbohydrate moieties on the xenograft with the sialic acid molecules having a concentration in a range of about 0.01 mM to about 100 mM.

5. The method of claim 4, wherein the soft tissue is selected from the group consisting of:

a) a medial or lateral meniscus from a knee joint;

b) a ligament or tendon c) an articular cartilage; and d) a combination thereof.

6. An article of manufacture comprising a substantially non-immunogenic soft tissue xenograft for implantation into a human, produced by the method of any one of claims 4 and 5.

7. A method of preparing a soft tissue xenograft for implantation into a human, which comprises the steps of:

a) removing at least a portion of a soft tissue from a non-human animal to provide a xenograft;

b) washing the xenograft in water and alcohol;

c) subjecting the xenograft to a cellular disruption treatment; and d) treating a plurality of surface carbohydrate moieties on the xenograft with a plurality of capping molecules to cap at least a portion of the surface carbohydrate moieties, whereby the xenograft is substantially non-immunogenic and has substantially the same mechanical properties as a corresponding portion of a native soft tissue;

wherein (i) the cellular disruption treatment comprises freeze/thaw cycling or exposure to gamma radiation; and (ii) the capping step comprises treating the surface carbohydrate moieties on the xenograft with the n-acetyl glucosamine molecules having a concentration in a range of about 0.01 mM to about 100 mM.

8. The method of claim 7, further comprises a step selected from the group consisting of:

a) prior to step c, piercing the xenograft;

b) following step c, treating the xenograft with a second enzyme;

c) following step c, treating the xenograft with one or more agents selected from the group consisting of anticalcification agents, antithrombotic agents, antibiotics, and growth factors;

d) following step c, sterilizing the xenograft;

e) following step c, treating the xenograft with polyethylene glycol;

f) following step c, exposing the xenograft to a crosslinking agent in a vapor form; and g) combinations thereof.

9. A method of preparing a soft tissue xenograft for implantation into a human, which comprises the steps of:

a) removing at least a portion of a soft tissue from a non-human animal to provide a xenograft;

b) washing the xenograft in water and alcohol;

c) subjecting the xenograft to a cellular disruption treatment; and d) treating a plurality of surface carbohydrate moieties on the xenograft with a plurality of capping molecules to cap at least a portion of the surface carbohydrate moieties, whereby the xenograft is substantially non-immunogenic and has substantially the same mechanical properties as a corresponding portion of a native soft tissue;

wherein (i) the cellular disruption treatment comprises freeze/thaw cycling or exposure to gamma radiation; and (ii) the capping step comprises treating the surface carbohydrate moieties on the xenograft with fucosyl molecules having a concentration in a range of about 0.01 mM to about 100 mM.

10. The method of claim 8, 7 or 9, wherein the soft tissue is selected from the group consisting of:

a) a medial or lateral meniscus from a knee joint;

b) a ligament or tendon;

c) an articular cartilage; and d) a combination thereof.

11. The method of claims 9 further comprises a step selected from the group consisting of:

a) prior to step c, piercing the xenograft;

b) following step c, treating the xenograft with a second enzyme;

c) following step c, treating the xenograft with one or more agents selected from the group consisting of anticalcification agents, antithrombotic agents, antibiotics, and growth factors;

d) following step c, sterilizing the xenograft;

e) following step c, treating the xenograft with polyethylene glycol;

f) following step c, exposing the xenograft to a crosslinking agent in a vapor form; and g) combinations thereof.

* * * * *